(12) United States Patent
Nassif et al.

(10) Patent No.: US 10,603,500 B2
(45) Date of Patent: Mar. 31, 2020

(54) METHODS AND SYSTEMS FOR FREQUENCY ADJUSTMENT TO OPTIMIZE CHARGING OF IMPLANTABLE NEUROSTIMULATOR

(71) Applicant: Axonics Modulation Technologies, Inc., Irvine, CA (US)

(72) Inventors: Rabih Nassif, Santa Ana, CA (US); Steve Hankins, San Diego, CA (US); Christopher J. Bowes, Laguna Hills, CA (US)

(73) Assignee: AXONICS MODULATION TECHNOLOGIES, INC., Irvine, CA (US)

( * ) Notice: Subject to any disclaimer, the term of this patent is extended or adjusted under 35 U.S.C. 154(b) by 108 days.

(21) Appl. No.: 15/416,888

(22) Filed: Jan. 26, 2017

(65) Prior Publication Data
US 2017/0216609 A1    Aug. 3, 2017

Related U.S. Application Data

(60) Provisional application No. 62/289,073, filed on Jan. 29, 2016.

(51) Int. Cl.
*H02J 7/00*      (2006.01)
*A61N 1/378*     (2006.01)
(Continued)

(52) U.S. Cl.
CPC ......... *A61N 1/3787* (2013.01); *A61N 1/3605* (2013.01); *H02J 7/0072* (2013.01);
(Continued)

(58) Field of Classification Search
USPC ................. 320/106, 107, 108, 109, 110, 112
See application file for complete search history.

(56) References Cited

U.S. PATENT DOCUMENTS 3,646,940 A    3/1972  Timm et al.
3,942,535 A    3/1976  Schulman et al.
(Continued)

FOREIGN PATENT DOCUMENTS

DE    102010006837 A1    8/2011
EP         1680182 B2    7/2006
(Continued)

OTHER PUBLICATIONS

Bosch et al., Sacral (S3) Segmental Nerve Stimulation As a Treatment for Urge Incontinence in Patients With Detrusor Instability: Results of Chronic Electrical Stimulation Using an Implantable Neural Prosthesis, The Journal of Urology, vol. 154, Aug. 1995, pp. 504-507.

(Continued)

*Primary Examiner* — Brian Ngo
(74) *Attorney, Agent, or Firm* — Kilpatrick Townsend & Stockton LLP

(57) ABSTRACT

Devices, systems, and methods for coupling with an implantable neurostimulator for delivering one or more electrical pulses to a target region within a patient's body are disclosed herein. A device, such as a charger, can include: a power source for storing electrical energy; a resonant circuit that can have a plurality of selectable natural frequencies; a driver coupled to the power source and the resonant circuit; and a processor coupled to the resonant circuit to control the natural frequency of the resonant circuit. The processor can control the natural frequency of the resonant circuit according to stored data associated with the implantable neurostimulator.

19 Claims, 15 Drawing Sheets

(51) Int. Cl.
*H02J 50/80* (2016.01)
*H02J 50/12* (2016.01)
*A61N 1/36* (2006.01)
*H02J 7/02* (2016.01)

(52) U.S. Cl.
CPC .............. *H02J 50/12* (2016.02); *H02J 50/80* (2016.02); *A61N 1/36007* (2013.01); *A61N 1/36107* (2013.01); *H02J 7/025* (2013.01)

(56) References Cited

U.S. PATENT DOCUMENTS

| | | |
|---|---|---|
| 4,019,518 A | 4/1977 | Sorenson et al. |
| 4,044,774 A | 8/1977 | Corbin et al. |
| 4,082,097 A | 4/1978 | Mann et al. |
| 4,340,062 A | 7/1982 | Thompson et al. |
| 4,468,723 A | 8/1984 | Hughes |
| 4,553,702 A | 11/1985 | Coffee et al. |
| 4,673,867 A | 6/1987 | Davis |
| 4,744,371 A | 5/1988 | Harris et al. |
| 5,143,089 A | 9/1992 | Alt |
| 5,193,539 A | 3/1993 | Schulman et al. |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras |
| 5,741,316 A | 4/1998 | Chen et al. |
| 5,876,423 A | 3/1999 | Braun et al. |
| 5,877,472 A | 3/1999 | Campbell et al. |
| 6,027,456 A | 2/2000 | Feler et al. |
| 6,035,237 A | 3/2000 | Schulman et al. |
| 6,052,624 A | 4/2000 | Mann et al. |
| 6,055,456 A | 4/2000 | Gerber |
| 6,057,513 A | 5/2000 | Tsuruta et al. |
| 6,067,474 A | 5/2000 | Schulman et al. |
| 6,076,017 A | 6/2000 | Taylor et al. |
| 6,104,960 A | 8/2000 | Duysens et al. |
| 6,164,284 A | 12/2000 | Schulman et al. |
| 6,172,556 B1 | 1/2001 | Prentice et al. |
| 6,178,353 B1 | 1/2001 | Griffith et al. |
| 6,185,452 B1 | 2/2001 | Schulman et al. |
| 6,191,365 B1 | 2/2001 | Avellanet et al. |
| 6,208,894 B1 | 3/2001 | Schulman et al. |
| 6,212,431 B1 | 4/2001 | Hahn et al. |
| 6,221,513 B1 | 4/2001 | Lasater et al. |
| 6,246,911 B1 | 6/2001 | Seligman |
| 6,249,703 B1 | 6/2001 | Stanton et al. |
| 6,265,789 B1 | 7/2001 | Hayakawa et al. |
| 6,306,100 B1 | 10/2001 | Prass et al. |
| 6,313,779 B1 | 11/2001 | Leung et al. |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner et al. |
| 6,516,227 B1 | 2/2003 | Mann et al. |
| 6,521,350 B2 | 2/2003 | Fey et al. |
| 6,564,807 B1 | 5/2003 | Schulman et al. |
| 6,584,355 B2 | 6/2003 | Stessman et al. |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,864,755 B2 | 3/2005 | Moore |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,986,453 B2 | 1/2006 | Jiang et al. |
| 6,989,200 B2 | 1/2006 | Schnittgrund et al. |
| 6,990,376 B2 | 1/2006 | Tanagho et al. |
| 6,999,819 B2 | 2/2006 | Swoyer et al. |
| 7,051,419 B2 | 5/2006 | Robinson et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer et al. |
| 7,167,749 B2 | 1/2007 | Biggs et al. |
| 7,177,690 B2 | 2/2007 | Thacker et al. |
| 7,177,698 B2 | 2/2007 | Park et al. |
| 7,181,286 B2 | 2/2007 | Sieracki et al. |
| 7,187,978 B2 | 3/2007 | Malek et al. |
| 7,191,005 B2 | 3/2007 | Stessman et al. |
| 7,212,110 B1 | 5/2007 | Martin et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,245,972 B2 | 7/2007 | Davis et al. |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,359,751 B1 | 4/2008 | Erickson et al. |
| 7,369,894 B2 | 5/2008 | Gerber et al. |
| 7,386,348 B2 | 6/2008 | Fowler et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Doan et al. |
| 7,450,991 B2 | 11/2008 | Smith et al. |
| 7,460,911 B2 | 12/2008 | Cosendai et al. |
| 7,463,928 B2 | 12/2008 | Torgerson et al. |
| 7,470,236 B1 | 12/2008 | Marino et al. |
| 7,483,752 B2 | 1/2009 | Von Arx et al. |
| 7,496,404 B2 | 2/2009 | Woods et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Nimmagadda et al. |
| 7,551,960 B2 | 6/2009 | Forsberg et al. |
| 7,555,346 B1 | 6/2009 | Loeb et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz et al. |
| 7,636,602 B2 | 12/2009 | Baru Fassio et al. |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | Colvin et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Torgerson et al. |
| 7,848,818 B2 | 12/2010 | Barolat et al. |
| 7,904,167 B2 | 3/2011 | Park et al. |

(56) References Cited

U.S. PATENT DOCUMENTS

| | | |
|---|---|---|
| 7,912,555 B2 | 3/2011 | Swoyer et al. |
| 7,925,357 B2 | 4/2011 | Phillips et al. |
| 7,932,696 B2 | 4/2011 | Peterson et al. |
| 7,933,656 B2 | 4/2011 | Sieracki et al. |
| 7,935,051 B2 | 5/2011 | Blewett et al. |
| 7,937,158 B2 | 5/2011 | Erickson et al. |
| 7,952,349 B2 | 5/2011 | Bono et al. |
| 7,957,818 B2 | 6/2011 | Swoyer et al. |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Blewett et al. |
| 8,000,805 B2 | 8/2011 | Swoyer et al. |
| 8,005,535 B2 | 8/2011 | Blewett et al. |
| 8,005,549 B2 | 8/2011 | Seifert et al. |
| 8,005,550 B2 | 8/2011 | Seifert et al. |
| 8,019,423 B2 | 9/2011 | Possover et al. |
| 8,024,047 B2 | 9/2011 | Olson et al. |
| 8,036,756 B2 | 10/2011 | Swoyer et al. |
| 8,044,635 B2 | 10/2011 | Peterson et al. |
| 8,050,769 B2 | 11/2011 | Blewett et al. |
| 8,055,337 B2 | 11/2011 | Moffitt et al. |
| 8,068,912 B2 | 11/2011 | Gharib et al. |
| 8,083,663 B2 | 12/2011 | Gross et al. |
| 8,103,360 B2 | 1/2012 | Foster et al. |
| 8,116,862 B2 | 2/2012 | Stevenson et al. |
| 8,121,701 B2 | 2/2012 | Loeb et al. |
| 8,129,942 B2 | 3/2012 | Choi et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink et al. |
| 8,175,717 B2 | 5/2012 | Feldman et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson et al. |
| 8,219,202 B2 | 7/2012 | Giftakis et al. |
| 8,233,990 B2 | 7/2012 | Goetz et al. |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom et al. |
| 8,340,786 B2 | 12/2012 | Gross et al. |
| 8,362,742 B2 | 1/2013 | Kallmyer et al. |
| 8,369,943 B2 | 2/2013 | Shuros et al. |
| 8,386,048 B2 | 2/2013 | Fister et al. |
| 8,417,346 B2 | 4/2013 | Giftakis et al. |
| 8,423,146 B2 | 4/2013 | Giftakis et al. |
| 8,447,402 B1 | 5/2013 | Antalfy et al. |
| 8,447,408 B2 | 5/2013 | North et al. |
| 8,457,756 B2 | 6/2013 | Rahman et al. |
| 8,457,758 B2 | 6/2013 | Olson et al. |
| 8,480,437 B2 | 7/2013 | Cook et al. |
| 8,494,625 B2 | 7/2013 | Hargrove et al. |
| 8,515,545 B2 | 8/2013 | Trier et al. |
| 8,538,530 B1 | 9/2013 | Orinski |
| 8,543,223 B2 | 9/2013 | Geroy et al. |
| 8,549,015 B2 | 10/2013 | Barolat et al. |
| 8,554,322 B2 | 10/2013 | Olson et al. |
| 8,555,894 B2 | 10/2013 | Schulman et al. |
| 8,562,539 B2 | 10/2013 | Marino et al. |
| 8,571,677 B2 | 10/2013 | Torgerson et al. |
| 8,577,474 B2 | 11/2013 | Feldman et al. |
| 8,588,917 B2 | 11/2013 | Whitehurst et al. |
| 8,612,002 B2 | 12/2013 | Faltys et al. |
| 8,620,436 B2 | 12/2013 | Parramon et al. |
| 8,620,454 B2 | 12/2013 | Bolea et al. |
| 8,626,314 B2 | 1/2014 | Swoyer et al. |
| 8,644,933 B2 | 2/2014 | Ozawa et al. |
| 8,655,451 B2 | 2/2014 | Park et al. |
| 8,655,453 B2 | 2/2014 | Werder et al. |
| 8,700,175 B2 | 4/2014 | Fell et al. |
| 8,706,254 B2 | 4/2014 | Mcclure et al. |
| 8,725,262 B2 | 5/2014 | Olson et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Nimmagadda et al. |
| 8,761,897 B2 | 6/2014 | Kaula et al. |
| 8,768,452 B2 | 7/2014 | Gerber et al. |
| 8,774,912 B2 | 7/2014 | Gerber et al. |
| 8,774,924 B2 | 7/2014 | Weiner et al. |
| 8,774,942 B2 | 7/2014 | Lund et al. |
| 8,805,524 B2 | 8/2014 | Loeb et al. |
| 8,918,174 B2 | 12/2014 | Peterson et al. |
| 8,954,148 B2 | 2/2015 | Cottrill et al. |
| 8,989,861 B2 | 3/2015 | Nelson et al. |
| 9,050,473 B2 | 6/2015 | Loeb et al. |
| 9,089,712 B2 | 7/2015 | Joshi et al. |
| 9,108,063 B2 | 8/2015 | Olson et al. |
| 9,149,635 B2 | 10/2015 | Denison et al. |
| 9,155,885 B2 | 10/2015 | Miesel et al. |
| 9,166,321 B2 | 10/2015 | Smith et al. |
| 9,166,441 B2 | 10/2015 | Dearden et al. |
| 9,168,374 B2 | 10/2015 | Su |
| 9,192,763 B2 | 11/2015 | Gerber et al. |
| 9,197,173 B2 | 11/2015 | Denison et al. |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Mcclure et al. |
| 9,248,292 B2 | 2/2016 | Trier et al. |
| 9,259,578 B2 | 2/2016 | Torgerson et al. |
| 9,259,582 B2 | 2/2016 | Floyd et al. |
| 9,265,958 B2 | 2/2016 | Joshi et al. |
| 9,270,134 B2 | 2/2016 | Gaddam et al. |
| 9,272,140 B2 | 3/2016 | Gerber et al. |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,314,616 B2 | 4/2016 | Wells et al. |
| 9,320,899 B2 | 4/2016 | Parramon et al. |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 2002/0116042 A1 | 8/2002 | Boling |
| 2003/0028072 A1 | 2/2003 | Fischell et al. |
| 2003/0040291 A1* | 2/2003 | Brewer .............. A61N 1/37223 455/127.1 |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2006/0016452 A1 | 1/2006 | Goetz et al. |
| 2006/0050539 A1 | 3/2006 | Yang et al. |
| 2006/0142822 A1 | 6/2006 | Tulgar et al. |
| 2006/0206166 A1 | 9/2006 | Weiner et al. |
| 2007/0073357 A1 | 3/2007 | Rooney et al. |
| 2007/0265675 A1 | 11/2007 | Lund et al. |
| 2007/0293914 A1 | 12/2007 | Woods et al. |
| 2008/0081962 A1 | 4/2008 | Miller et al. |
| 2008/0132961 A1 | 6/2008 | Jaax et al. |
| 2008/0172109 A1 | 7/2008 | Rahman et al. |
| 2008/0183236 A1 | 7/2008 | Gerber et al. |
| 2008/0278974 A1 | 11/2008 | Wu |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2009/0284220 A1 | 11/2009 | Toncich et al. |
| 2010/0076254 A1 | 3/2010 | Jimenez et al. |
| 2010/0076534 A1 | 3/2010 | Mock et al. |
| 2010/0331918 A1 | 12/2010 | DiGiore et al. |
| 2011/0101790 A1 | 5/2011 | Budgett |
| 2011/0152959 A1 | 6/2011 | Sherwood et al. |
| 2011/0270269 A1 | 11/2011 | Swoyer et al. |

(56) References Cited

U.S. PATENT DOCUMENTS

| | | |
|---|---|---|
| 2011/0278948 A1 | 11/2011 | Forsell |
| 2011/0282416 A1 | 11/2011 | Hamann et al. |
| 2011/0288615 A1* | 11/2011 | Armstrong ............ A61B 5/0031 607/59 |
| 2011/0301667 A1 | 12/2011 | Olson et al. |
| 2011/0313427 A1 | 12/2011 | Gindele et al. |
| 2012/0016447 A1 | 1/2012 | Zhu et al. |
| 2012/0041512 A1 | 2/2012 | Weiner et al. |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0139485 A1 | 6/2012 | Olson et al. |
| 2012/0235634 A1 | 9/2012 | Hall et al. |
| 2012/0259381 A1 | 10/2012 | Smith et al. |
| 2012/0262108 A1 | 10/2012 | Olson et al. |
| 2012/0267960 A1 | 10/2012 | Low et al. |
| 2012/0274270 A1 | 11/2012 | Dinsmoor et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0096651 A1 | 4/2013 | Ozawa et al. |
| 2013/0148768 A1 | 6/2013 | Kim |
| 2013/0150925 A1 | 6/2013 | Vamos et al. |
| 2013/0197608 A1 | 8/2013 | Eiger et al. |
| 2013/0211479 A1 | 8/2013 | Olson et al. |
| 2013/0303942 A1 | 11/2013 | Damaser et al. |
| 2013/0310630 A1 | 11/2013 | Smith et al. |
| 2013/0310894 A1 | 11/2013 | Trier et al. |
| 2013/0331909 A1 | 12/2013 | Gerber et al. |
| 2013/0331910 A1 | 12/2013 | Lamont et al. |
| 2014/0031903 A1 | 1/2014 | Mashiach |
| 2014/0107743 A1 | 4/2014 | Wahlstrand et al. |
| 2014/0207220 A1 | 7/2014 | Boling et al. |
| 2014/0222112 A1 | 8/2014 | Fell et al. |
| 2014/0237806 A1 | 8/2014 | Smith et al. |
| 2014/0277268 A1 | 9/2014 | Lee et al. |
| 2014/0277270 A1 | 9/2014 | Parramon et al. |
| 2015/0088227 A1 | 3/2015 | Shishilla et al. |
| 2015/0094790 A1 | 4/2015 | Shishilla et al. |
| 2015/0100106 A1 | 4/2015 | Shishilla et al. |
| 2015/0134027 A1 | 5/2015 | Kaula et al. |
| 2015/0214604 A1 | 7/2015 | Zhao et al. |
| 2015/0335888 A1* | 11/2015 | Demers ................ A61N 1/0456 607/45 |
| 2015/0335893 A1 | 11/2015 | Parker |
| 2016/0022996 A1 | 1/2016 | Kaula et al. |
| 2016/0114177 A1 | 4/2016 | Colvin et al. |
| 2016/0126771 A1 | 5/2016 | Aghassian et al. |
| 2016/0199658 A1* | 7/2016 | Nassif ................ A61N 1/36125 607/60 |

FOREIGN PATENT DOCUMENTS

| | | |
|---|---|---|
| EP | 1904153 | 4/2008 |
| EP | 2243509 | 10/2010 |
| EP | 2498873 A2 | 9/2012 |
| EP | 2731673 | 5/2014 |
| JP | 2003047179 A | 2/2003 |
| WO | WO 2000/56677 | 9/2000 |
| WO | WO 2000/066221 A1 | 11/2000 |
| WO | WO 2002/003408 A2 | 1/2002 |
| WO | WO 2002/009808 A1 | 2/2002 |
| WO | WO 2004/103465 A1 | 12/2004 |
| WO | WO 2008/021524 | 2/2008 |
| WO | WO 2009/051539 A1 | 4/2009 |
| WO | WO 2009/091267 A2 | 7/2009 |
| WO | WO 2010/042056 A1 | 4/2010 |
| WO | WO 2010/042057 A1 | 4/2010 |
| WO | WO 2011/059565 | 5/2011 |
| WO | WO 2013/141884 | 9/2013 |

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994 (Jan. 1, 1994), pp. 148-152.

Ghovanloo et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Gudnason, G., "A low-power ASK demodulator for Inductively coupled implantable electronics", Solid-State Circuits Conference, 2000, Esscirc "00, Proceedings of the 26RD European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, (Mar. 1, 2005), pp. 763-771.

Tanagho et al., Bladder Pacemaker: Scientific Basis and Clinical Future, Urology, vol. 20, No. 6, Dec. 1982, pp. 614-619.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006 (Dec. 1, 2006), pp. 696-699.

U.S. Appl. No. 14/446,294, filed Jul. 29, 2014.

Paralikar., et al., A Fully Implantable and Rechargeable Neurostimulation System for Animal Research, 7th Annual International IEEE EMBS Conference of Neural Engineering, Montpellier, France, Apr. 22-24, 2015, pp. 418-421.

\* cited by examiner methods and systems for FREQUENCY ADJUSTMENT TO OPTIMIZE CHARGING OF IMPLANTABLE NEUROSTIMULATOR

CROSS-REFERENCES TO RELATED APPLICATIONS

The present application is a non-provisional of and claims the benefit of priority of U.S. Provisional Application No. 62/289,073 filed on Jan. 29, 2016, and entitled "Methods and Systems for Frequency Adjustment to Optimize Charging of Implantable Neurostimulator," the entirety of which is hereby incorporated by reference herein.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, frequency, and/or voltage that is effective to affect a body function for one patent may impose significant pain on, or have limited effect for, another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

The effectiveness of such current stimulation systems relies heavily on the ability to maintain a charge in an implanted neurostimulator. This requires effective charging of the implanted neurostimulator. However, due to complexities arising from charging an implanted device, the coupling of the implanted neurostimulator and a charger is not always effective or efficient. This leads to problems such as excess heating of the implanted neurostimulator and/or of tissue surrounding the implanted neurostimulator.

The tremendous benefits of these neural stimulation therapies have not yet been fully realized. Therefore, it is desirable to provide improved neurostimulation methods, systems and devices, as well as methods for implanting and configuring such neurostimulation systems for a particular patient or condition being treated. It would be particularly helpful to provide such systems and methods so as to improve ease of use by the physician in implanting and configuring the system, as well as to improve patient comfort and alleviation of symptoms for the patient, and/or to provide improved charging features or charging methods.

BRIEF SUMMARY OF THE INVENTION

One aspect of the present disclosure relates to a charger for coupling with an implantable neurostimulator for delivering one or more electrical pulses to a target region within a patient's body. The charger includes: a power source for storing electrical energy; a resonant circuit that can be configured to have a plurality of natural frequencies; a driver coupled to the power source and the resonant circuit, which driver can power the resonant circuit; and a processor coupled to the resonant circuit to control the natural frequency of the resonant circuit. In some embodiments, the processor can control the natural frequency of the resonant circuit according to stored data associated with the implantable neurostimulator.

In some embodiments, controlling the natural frequency of the resonant circuit according to stored data associated with the implantable neurostimulator includes: receiving identifying data from the implantable neurostimulator; and retrieving characterization data, which characterization identifies a natural frequency of a resonant circuit of the implantable neurostimulator. In some embodiments, controlling the natural frequency of the resonant circuit according to stored data associated with the implantable neurostimulator includes: detecting a first natural frequency of the resonant circuit of the charger; comparing the first natural frequency of the resonant circuit of the charger to the characterization data; and changing the natural frequency of the resonant circuit of the charger from the first natural frequency to a second natural frequency. In some embodiments, detecting the first natural frequency of the resonant circuit of the charger includes at least one of: determining the driving frequency of the driver; or detecting ringing of the resonant circuit. In some embodiments, the second natural frequency corresponds to the characterization data.

In some embodiments, the resonant circuit includes: an inductor; a first capacitor coupled in series to the inductor; and a plurality of capacitors switchably coupleable to the inductor, which plurality of capacitors are each configured to be in parallel with the first capacitor when switchably coupled to the inductor. In some embodiments, the plurality of capacitors includes three capacitors. In some embodiments, each of the plurality of capacitors is switchably coupleable to the inductor via a transistor. In some embodiments, the transistor is a field effect transistor.

In some embodiments, changing the natural frequency of the resonant circuit of the charger from the first natural frequency to a second natural frequency includes: identifying a first switch configuration of the resonant circuit resulting in the first natural frequency; identifying a second switch configuration of the resonant circuit resulting in the second natural frequency; and generating a control signal to control at least one of: the opening of at least one switch in the resonant circuit to disconnect at least one of the plurality of capacitors from the inductor; or the closing of at least one switch in the resonant circuit to connect at least one of the plurality of capacitors from the inductor. In some embodiments, changing the natural frequency of the resonant circuit of the charger from the first natural frequency to a second natural frequency includes: identifying a first inductance of an inductor in the resonant circuit resulting in the first natural frequency; identifying a second inductance of the inductor in the resonant circuit resulting in the second natural frequency; and generating a control signal to change the inductance of the inductor from the first inductance to the second inductance.

In some embodiments, changing the inductance of the inductor from the first inductance to the second inductance includes changing a saturation level of a core of the inductor from a first saturation level to a second saturation level. In some embodiments, changing the saturation level of the core of the inductor from the first saturation level to the second saturation level includes changing a voltage applied the core of the inductor from a first voltage to a second voltage.

In some embodiments, the first natural frequency is repeatedly detected, and in some embodiments, the first natural frequency is periodically detected. In some embodiments, the natural frequency of the resonant circuit can be adjusted within a range of 20 Hz. In some embodiments, the natural frequency of the resonant circuit can be adjusted within a range of 10 Hz. In some embodiments, the natural frequency of the resonant circuit can be adjusted between approximately 119 Hz and 130 Hz. In some embodiments, the driver includes a class-E driver. In some embodiments, the stored data associated with the implantable neurostimulator identifies the implantable neurostimulator and/or the stored data associated with the implantable neurostimulator identifies a previously determined natural frequency of the implantable neurostimulator.

One aspect of the present disclosure relates to a neurostimulation system for delivering one or more electrical pulses to a target region within a patient's body. The neurostimulation system includes: an implantable neurostimulator including: a hermetic housing having an external surface that is implantable within a body of a patient, the housing including a ceramic transmission region; and a charging circuit that can receive power through the ceramic region of the hermetic housing. The system can include a charger for coupling with an implantable neurostimulator, the charger including: a resonant circuit, which resonant circuit is configurable to a plurality of natural frequencies; and a processor coupled to the resonant circuit to control the natural frequency of the resonant circuit according to stored data identifying a previously determined natural frequency of the charging circuit of the implantable neurostimulator.

In some embodiments, the processor can control the natural frequency of the resonant circuit according to characterization data identifying a natural frequency of the charging circuit of the implantable neurostimulator. In some embodiments, the characterization data is uniquely associated with the implantable neurostimulator, and the characterization data is stored in a database in memory at the charger. In some embodiments, the characterization data is received at the charger from the implantable neurostimulator when the charger is coupled with the implantable neurostimulator. In some embodiments, the characterization data is generated by the charger when the database does not contain characterization data for the implantable neurostimulator.

In some embodiments, generating the characterization data includes: controlling the natural frequency of the resonant circuit to iteratively cycle through a plurality of natural frequencies of the resonant circuit; iteratively receiving data from the implantable neurostimulator indicative of a level of matching between the plurality of natural frequencies of the resonant circuit and a natural frequency of the charging circuit of the implantable neurostimulator; and identifying one of the plurality of natural frequencies as the natural frequency of the charging circuit of the implantable neurostimulator.

In some embodiments, the identified one of the plurality of natural frequencies is the one of the plurality of natural frequencies that best matches the natural frequency of the charging circuit of the implantable neurostimulator. In some embodiments, the identified one of the plurality of natural frequencies is the one of the plurality of natural frequencies that best matches the natural frequency of the charging circuit of the implantable neurostimulator over a statistically significant number of iterations. In some embodiments, the identified one of the plurality of natural frequencies is a default natural frequency.

One aspect of the present disclosure relates to a method for coupling a charger with an implantable neurostimulator for delivering one or more electrical pulses to a target region within a patient's body. The method includes: powering a resonant circuit of a charger with a driver coupled to a power source, which resonant circuit is configurable to a plurality of natural frequencies; determining a first natural frequency of the resonant circuit; retrieving stored characterization data, which characterization identifies a previously determined natural frequency of a resonant circuit of the implantable neurostimulator; and changing the natural frequency of the resonant circuit from the first natural frequency to a second natural frequency with control signals generated by a processor according to the characterization data.

In some embodiments, determining the natural frequency of the resonant circuit of the charger includes at least one of: determining the driving frequency of the driver; or detecting ringing of the resonant circuit. In some embodiments, the resonant circuit includes: an inductor; a first capacitor coupled in series to the inductor; and a plurality of capacitors switchably coupleable to the inductor, which plurality of capacitors can be in parallel with the first capacitor when switchably coupled to the inductor. In some embodiments, the plurality of capacitors includes three capacitors. In some embodiments, each of the plurality of capacitors is switchably coupleable to the inductor via a transistor.

In some embodiments, changing the natural frequency of the resonant circuit of the charger from the first natural frequency to a second natural frequency includes: identifying a first switch configuration of the resonant circuit resulting in the first natural frequency; identifying a second switch configuration of the resonant circuit resulting in the second natural frequency; and generating a control signal to control at least one of: the opening of at least one switch in the resonant circuit to disconnect at least one of the plurality of capacitors from the inductor; or the closing of at least one switch in the resonant circuit to connect at least one of the plurality of capacitors from the inductor. In some embodiments, changing the natural frequency of the resonant circuit of the charger from the first natural frequency to a second natural frequency includes: identifying a first inductance of an inductor in the resonant circuit resulting in the first natural frequency; identifying a second inductance of the inductor in the resonant circuit resulting in the second natural frequency; and generating a control signal to change the inductance of the inductor from the first inductance to the second inductance.

In some embodiments, the characterization data is retrieved from a database in memory at the charger. In some embodiments, the characterization data is generated by the charger. In some embodiments, generating the characterization data includes: controlling the natural frequency of the resonant circuit to iteratively cycle through a plurality of natural frequencies of the resonant circuit; iteratively receiving data from the implantable neurostimulator indicative of a level of matching between the plurality of natural frequencies of the resonant circuit and a natural frequency of the charging circuit of the implantable neurostimulator; and identifying one of the plurality of natural frequencies as the natural frequency of the charging circuit of the implantable neurostimulator.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION OF THE INVENTION

Figure 1:
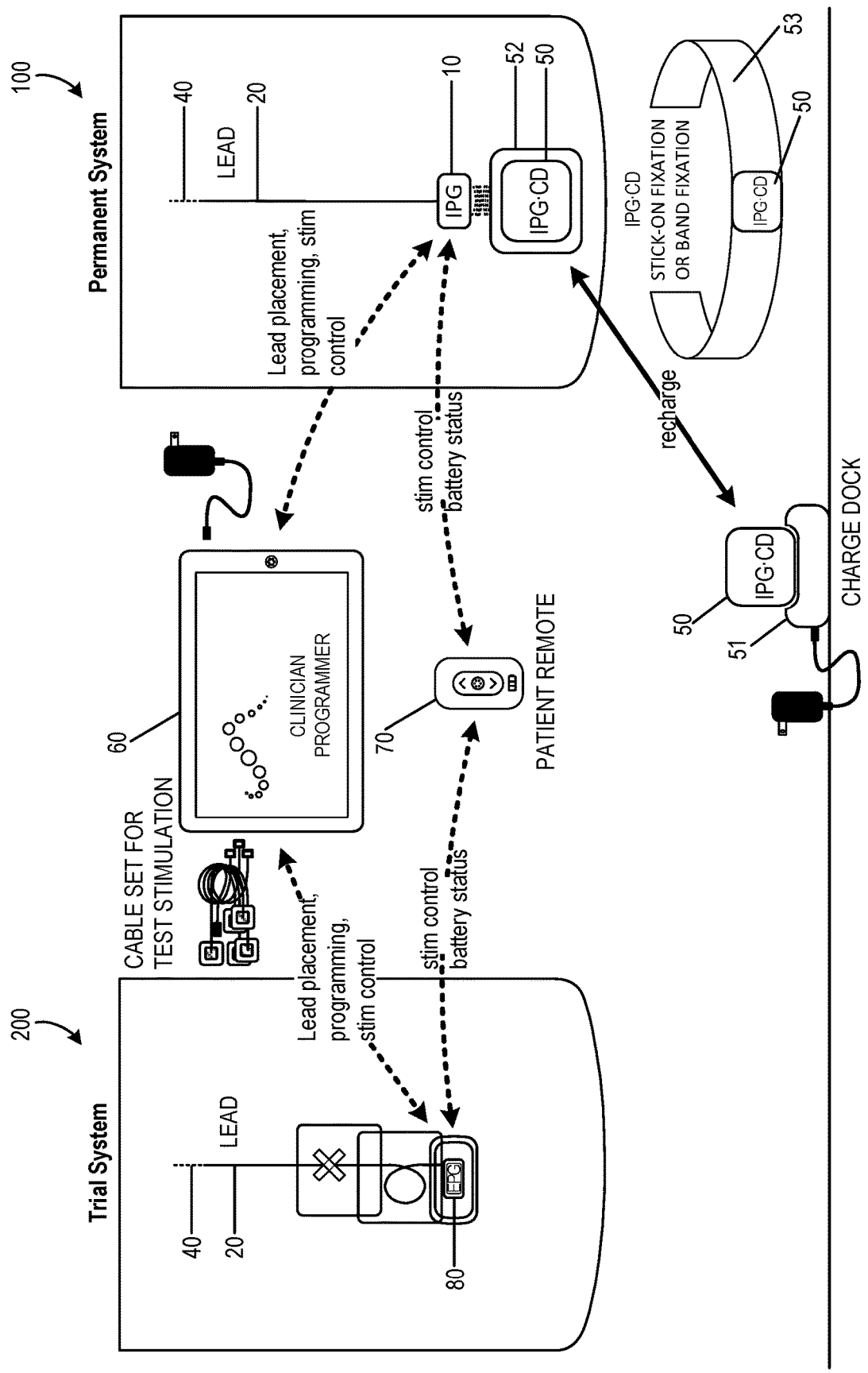
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In one particular embodiment, the invention relates to sacral nerve stimulation treatment systems configured to treat overactive bladder ("OAB") and relieve symptoms of bladder related dysfunction. It will be appreciated, however, that the present invention may also be utilized for any variety of neuromodulation uses, such as fecal dysfunction, the treatment of pain or other indications, such as movement or affective disorders, as will be appreciated by one of skill in the art.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of Botulinum Toxin (BoNT-A), Percutaneous Tibial Nerve Stimulation (PTNS) and Sacral Nerve Stimulation (SNM). BoNT-A (Botox®) is administered via a series of intradetrusor injections under cystoscopic guidance, but repeat injections of Botox are generally required every 4 to 12 months to maintain effect and Botox may undesirably result in urinary retention. A number of randomized controlled studies have shown some efficacy of BoNT-A in OAB patients, but long-term safety and effectiveness of BoNT-A for OAB is largely unknown.

Alternative treatment methods, typically considered when the above approaches prove ineffective, is neurostimulation of nerves relating to the urinary system. Such neurostimulation methods include PTNS and SNM. PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies; however, long-term safety and effectiveness of PTNS are relatively unknown at this time.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, are supported by multiple studies and are well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
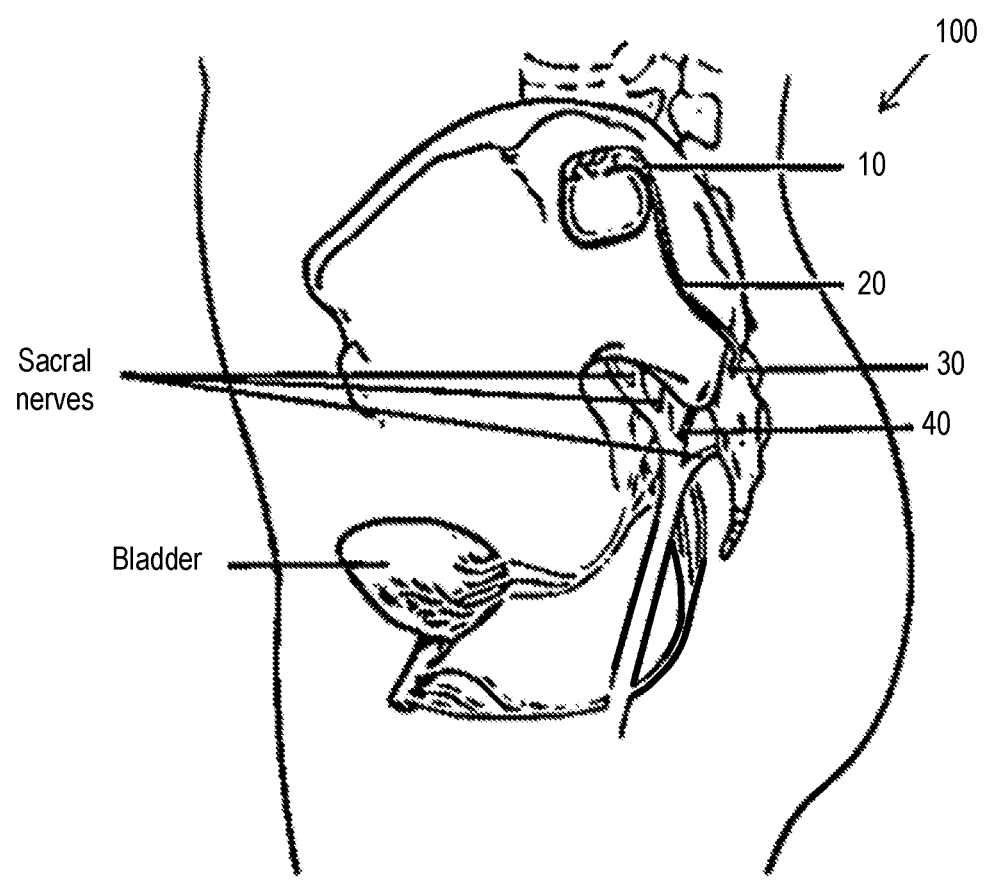
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| | Nerve Innervation | Response | | |
|---|---|---|---|---|
| | | Pelvic Floor | Foot/calf/leg | Sensation |
| S2 | Primary somatic contributor of pudendal nerve for external sphincter, leg, foot | "clamp"* of anal sphincter | Leg/hip rotation, plantar flexion of entire foot, contraction of calf | Contraction of base of penis, vagina |
| S3 | Virtullay all pelvic autonomic functions and striated muscle (levator ani) | "bellows"** of perineum | Plantar flexion of great toe, occasionally other toes | Pulling in rectum, extending forward to scrotum or labia |
| S4 | Pelvic autonomic and somatic No leg or foot | "bellows"** | No lower extremity motor stimulation | Pulling in rectum only |

*Clamp: contraction of anal sphincter and, in males, retraction of base of penis. Move buttocks aside and look for anterior/posterior shortening of the perineal structures.
**Bellows: lifting and dropping of pelvic floor. Look for deepersing and flattening of buttock groove.

In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupts, inhibits, or prevents neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

B. Positioning Neurostimulation Leads with EMG

While conventional approaches have shown efficacy in treatment of bladder related dysfunction, there exists a need to improve positioning of the neurostimulation leads and consistency between the trial and permanent implantation positions of the lead. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract), in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measureable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measureable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example Embodiments

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the clinician programmer 60 is used by a physician to adjust the settings of the EPG and/or IPG while the lead is implanted within the patient. The clinician programmer can be a tablet computer used by the clinician to program the IPG, or to control the EPG during the trial period. The clinician programmer can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface, an EMG module, electrical contacts such as an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the clinician programmer may be configured for coupling with an electrical ground or ground patch, an electrical pulse generator (e.g., an EPG or an IPG), or the like. As noted above, the clinician programmer can include a module with hardware and computer-code to execute EMG analysis, where the module can be a component of the control unit microprocessor, a pre-processing unit coupled to or in-line with the stimulation and/or sensory cables, or the like.

In some aspects, the clinician programmer is configured to operate in combination with an EPG when placing leads in a patient body. The clinician programmer can be electronically coupled to the EPG during test simulation through a specialized cable set. The test simulation cable set can connect the clinician programmer device to the EPG and allow the clinician programmer to configure, modify, or otherwise program the electrodes on the leads connected to the EPG.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
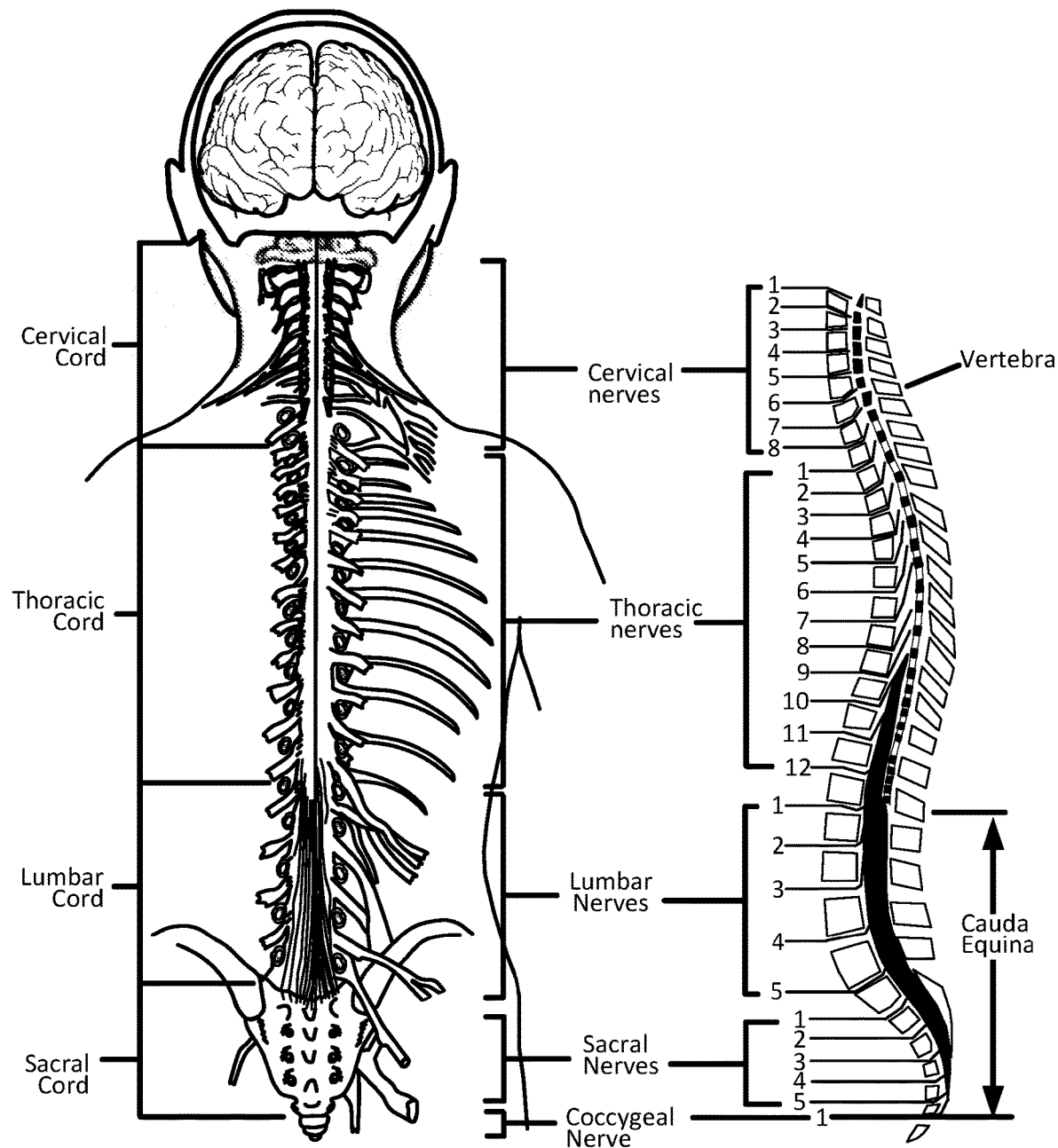
FIGS. 2A-2C show diagrams of the nerve structures along the spine, the lower back and sacrum region, which may be stimulated in accordance with aspects of the invention.
Figure 2B:
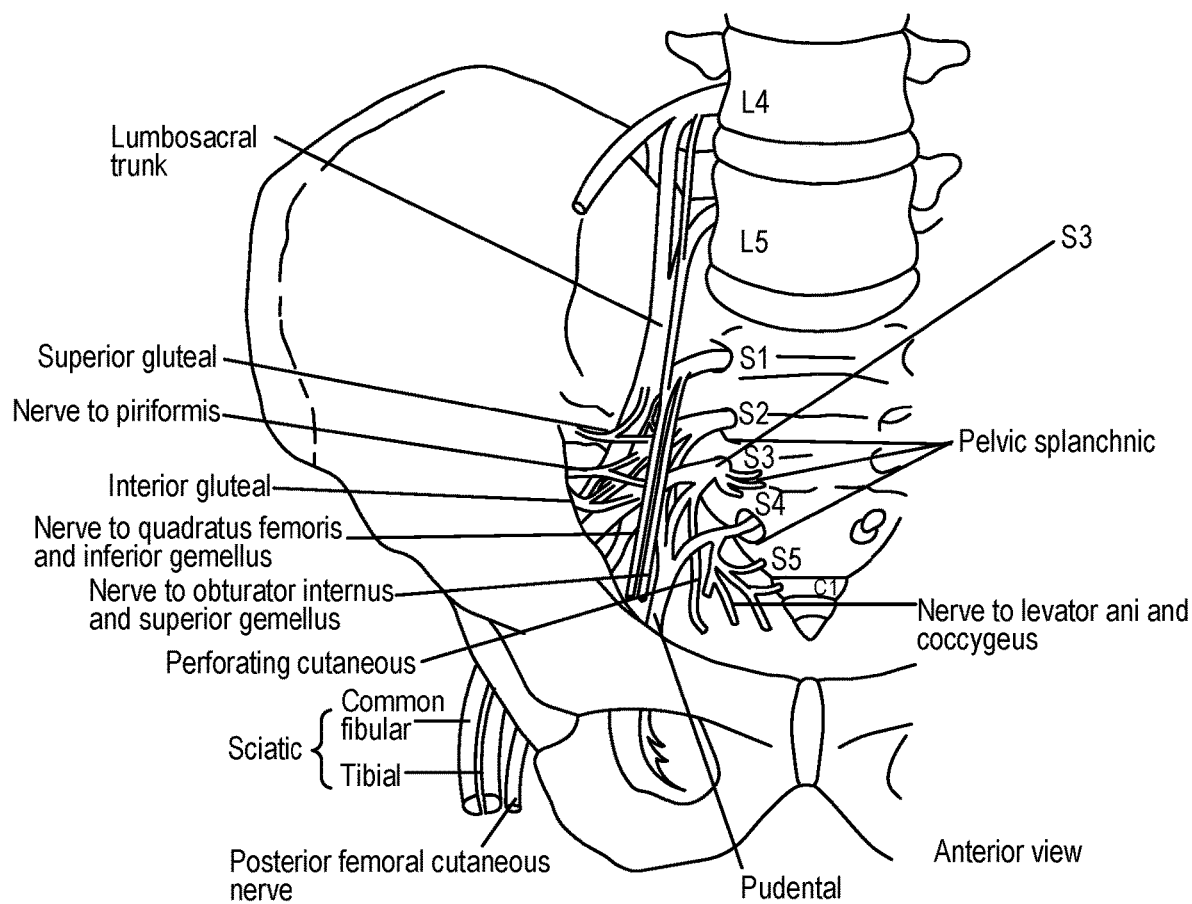
Figure 2C:
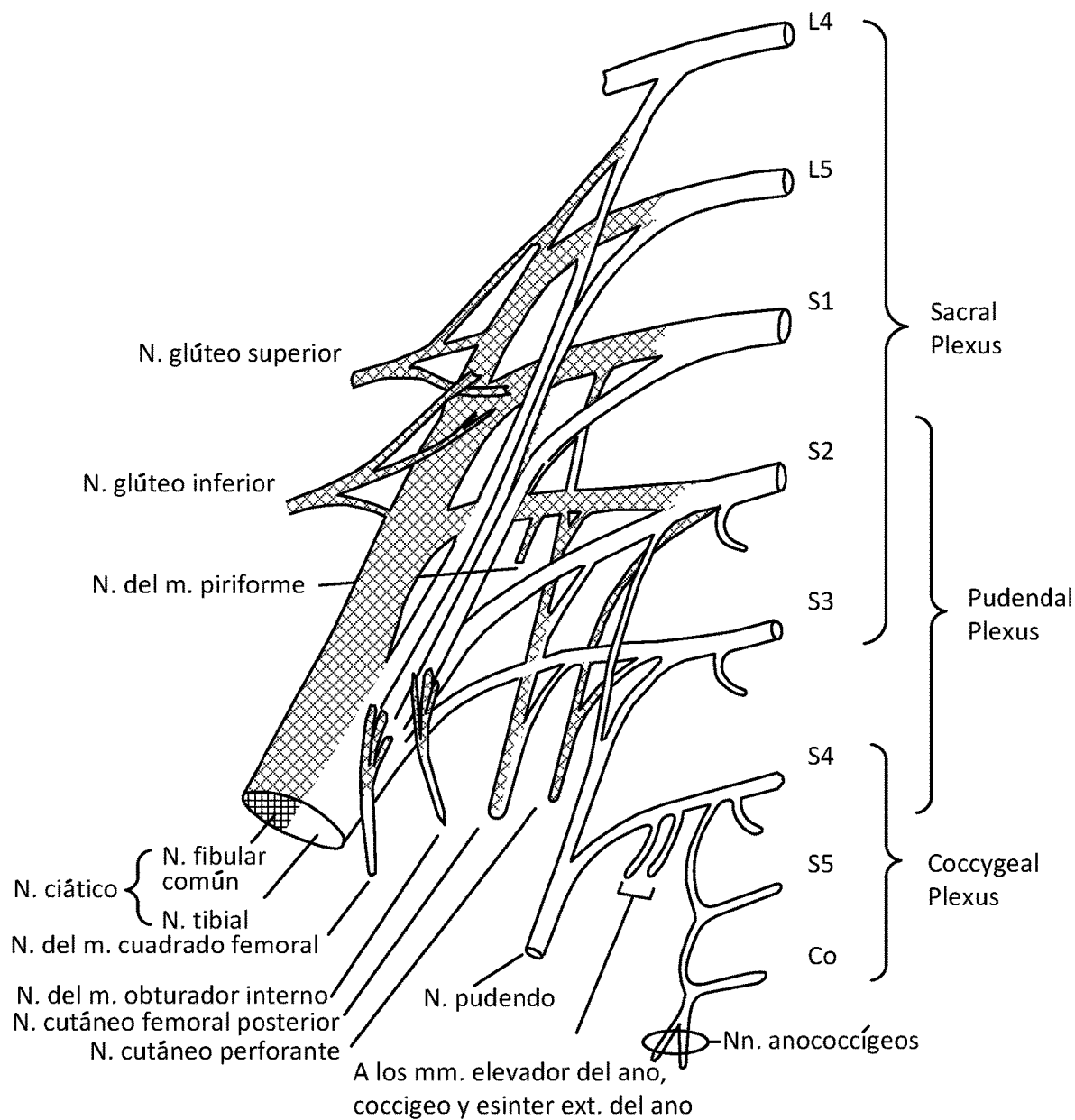

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain threshold may trigger the noted muscle responses, stimulation at a sub-threshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder-related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
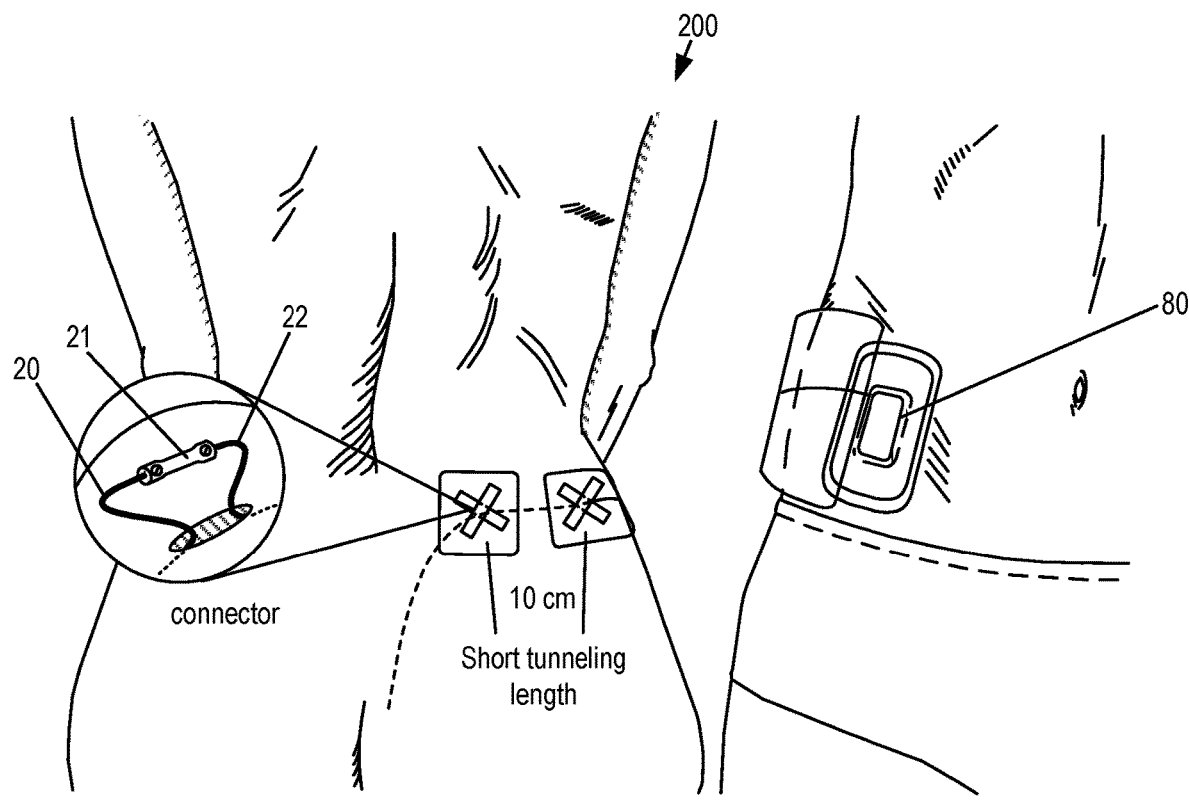
FIG. 3B shows an example of a neurostimulation system having a partly implanted stimulation lead and an external pulse generator adhered to the skin of the patient for use in a trial stimulation, in accordance with aspects of the invention.
Figure 3B:
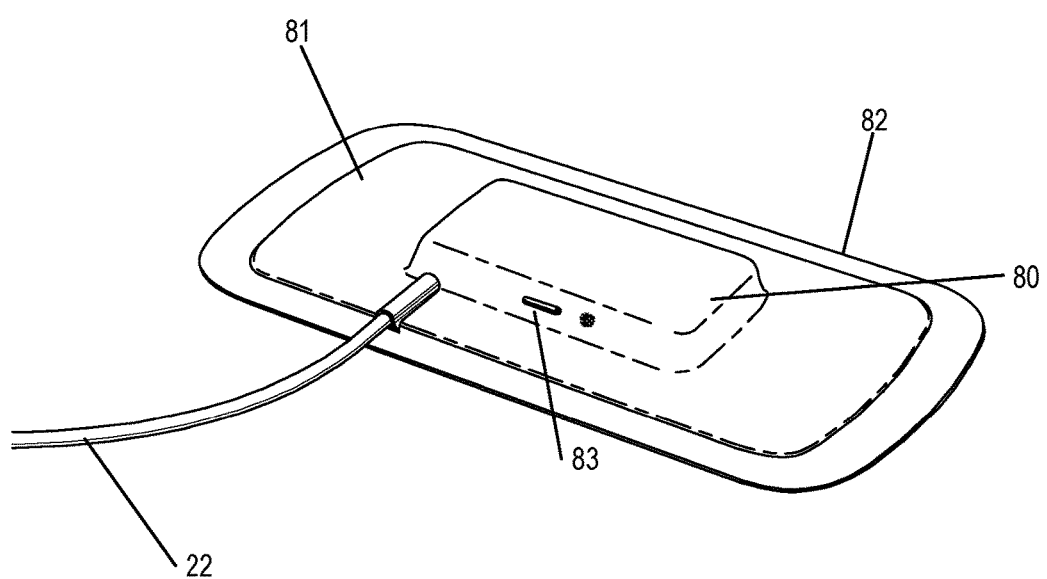

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the clinician programmer using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) therebetween. This technique may also minimize movement of an implanted lead during conversion of the trial system to a permanently implanted system.

In one aspect, the EPG unit is wirelessly controlled by a patient remote and/or the clinician programmer in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The clinician programmer can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

As shown in the detailed view of FIG. 3B, the EPG 80 is encased within a flexible laminated patch 81, which includes an aperture or port through which the EPG 80 is connected to the lead extension 22. The patch may further include an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

Figure 4:
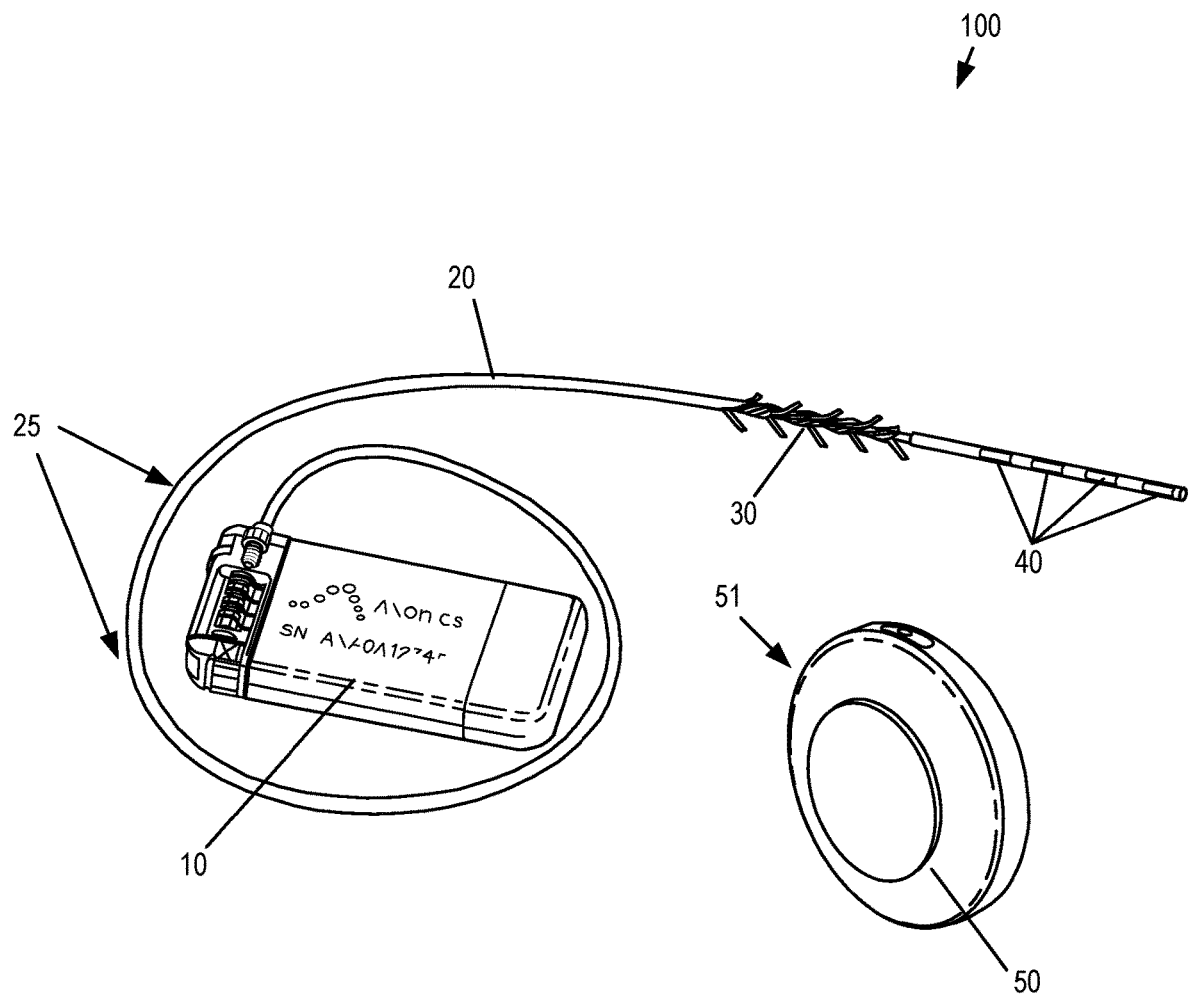
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

In one aspect, the IPG is rechargeable wirelessly through conductive coupling by use of a charging device 50 (CD), which is a portable device powered by a rechargeable battery to allow patient mobility while charging. The CD 50 is used for transcutaneous charging of the IPG through RF induction. The CD 50 can either be either patched to the patient's skin using an adhesive or can be held in place using a belt 53 or by an adhesive patch 52. The CD 50 may be charged by plugging the CD directly into an outlet or by placing the CD in a charging dock or station 51 that connects to an AC wall outlet or other power source.

The CD 50 can include a housing 51. The housing 51 can comprise a variety of shapes and sizes. In some embodiments, the housing 51 can be cylindrically shaped as shown in FIG. 4, and specifically, can comprise a plurality of connected cylindrical portions, wherein the connected cylindrical portions have different diameters and/or lengths. In some embodiments, the housing 51 can be a metal or polymer such as a plastic or the like.

The CD 50 can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. The CD 50 may include an energy storage feature, such as one or more capacitors, and typically includes a wireless charging unit. Some details of CD 50 will be discussed at greater lengths below with respect to FIG. 7.

The system may further include a patient remote 70 and clinician programmer 60, each configured to wirelessly communicate with the implanted IPG, or with the EPG during a trial. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
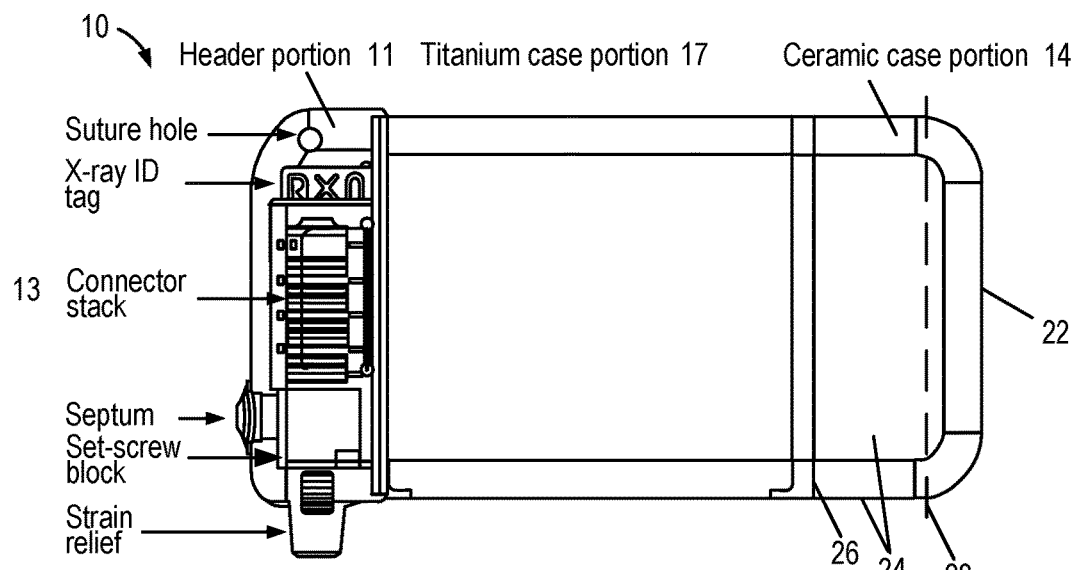
FIGS. 5A-5C show detail views of an implantable pulse generator and associated components for use in a neurostimulation system, in accordance with aspects of the invention.
Figure 5B:
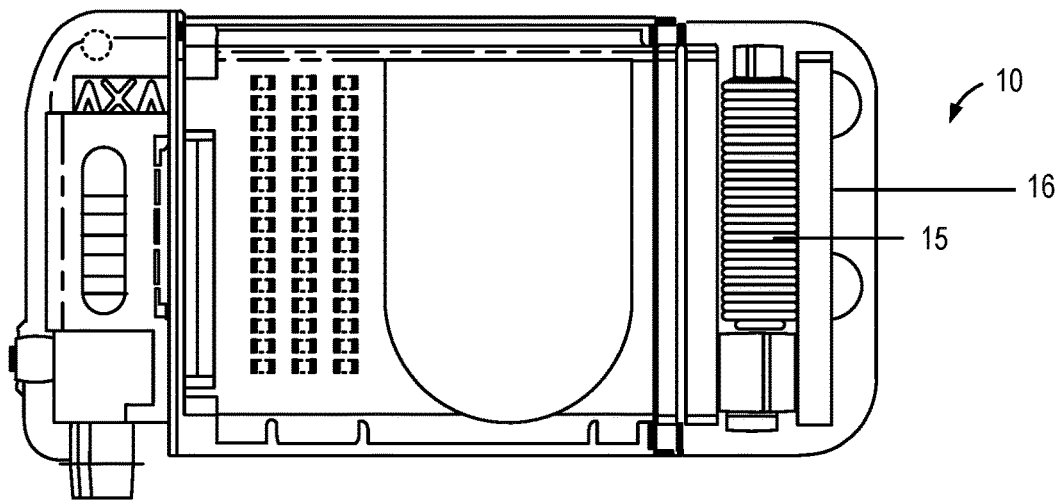
Figure 5C:
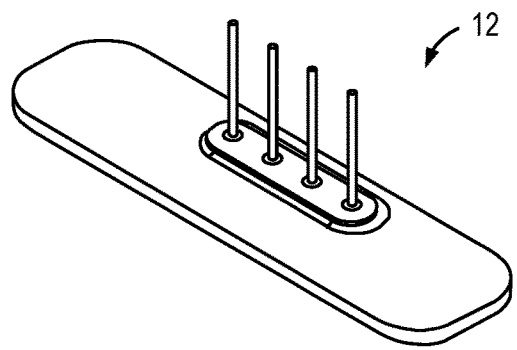

FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 100 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 μs to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed-through assembly 12 and connector stack 13, while the ceramic case portion 14 houses an antennae assembly 16 to facilitate wireless communication with the clinician program, the patient remote, and/or a charging coil to facilitate wireless charging with the CD. The remainder of the IPG is covered with a titanium case portion 17, which encases the printed circuit board, memory and controller components that facilitate the electrical pulse programs described above. The ceramic portion 14 includes an end 22, sides 24, and a connection portion 26 that connects the ceramic portion 14 to the case portion 17. In the example shown in FIG. 5B, the antennae assembly 16 is positioned such that a plane 28, in which loops of a radiating element lay, is perpendicular to and extends through the sides 24 of the ceramic portion 14.

In the example shown in FIG. 5C, the header portion of the IPG includes a four-pin feed-through assembly 12 that couples with the connector stack 13 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics. In some embodiments, some or all of the pieces of the IPG 10 forming the hermetic housing can be biocompatible, and specifically, can have external surfaces made of biocompatible materials.

In some embodiments, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG, and that ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at a depth of 3 cm with the CD, when positioned on a skin surface of the patient near the IPG, and reduces re-charging time.

Figure 6:
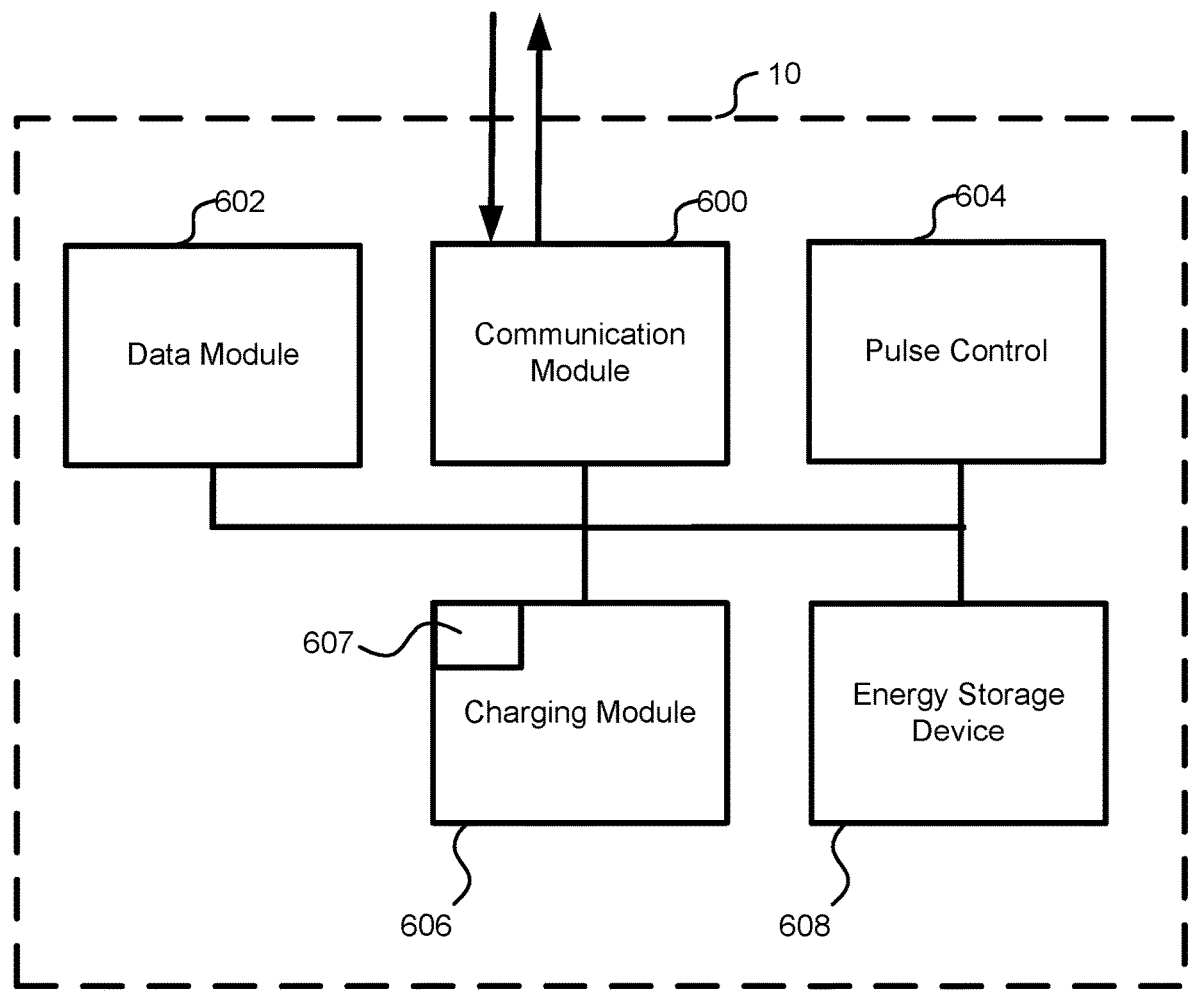
FIG. 6 shows a schematic illustration of one embodiment of the architecture of the IPG.

FIG. 6 shows a schematic illustration of one embodiment of the architecture of the IPG 10. In some embodiments, each of the components of the architecture of the IPG 10 can be implemented using the processor, memory, and/or other hardware component of the IPG 10. In some embodiments, the components of the architecture of the IPG 10 can include software that interacts with the hardware of the IPG 10 to achieve a desired outcome, and the components of the architecture of the IPG 10 can be located within the housing.

In some embodiments, the IPG 10 can include, for example, a communication module 600. The communication module 600 can be configured to send data to and receive data from other components and/or devices of the exemplary nerve stimulation system including, for example, the clinician programmer 60, the charging device 50, and/or the patient remote 70. In some embodiments, the communication module 600 can include one or several antennas and software configured to control the one or several antennas to send information to and receive information from one or several of the other components of the IPG 10. In some embodiments, for example, when connecting with the charging device 50, the communications module 600 can be configured to send data identifying the IPG 10 and/or characterizing one or several attributes of the IPG 10. In some embodiments, this information can be, for example, a number uniquely identifying the IPG 10 such as, for example, a serial number, or the like. In some embodiments, this data can characterize one or several attributes of the IPG 10 such as, for example, the natural frequency of a charging module 606 of the IPG 10 and/or of one or several components of the charging module 606 of the IPG.

The IPG 10 can further include a data module 602. The data module 602 can be configured to manage data relating to the identity and properties of the IPG 10. In some embodiments, the data module can include one or several databases that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like. In some embodiments, the information associated with the property of the IPG 10 can include, for example, data identifying the natural frequency of the IPG 10 and/or components thereof. In some embodiments, this information identifying the natural frequency can be generated at the time of the manufacture of the IPG 10.

The IPG 10 can include a pulse control 604. In some embodiments, the pulse control 604 can be configured to control the generation of one or several pulses by the IPG 10. In some embodiments, for example, this can be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, information relating to and/or for controlling the pulse generation of the IPG 10 can be stored within the memory.

The IPG 10 can include a charging module 606. In some embodiments, the charging module 606 can be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charging device 50 to create an inductive coupling to thereby recharge the IPG 10. In some embodiments, the charging module 606 can include hardware and/or software configured to monitor the charging of the IPG 10 including, for example, the charging coil assembly 15.

The charging module 606 of the IPG 10 can include a charging circuit 607, also referred to herein as the resonant circuit 607, the secondary charging circuit 607, the secondary resonant circuit 607, the receiving charging circuit 607, or the receiving resonant circuit 607. In some embodiments, the charging circuit 607 can comprise, for example, at least one of: an inductor; a capacitor; or a resistor. The charging circuit 607 can be characterized by a natural frequency, which natural frequency can be determined at, for example, the time of assembly of the charging circuit 607 or after the implantation of the IPG 10 in the body. In some embodiments, because of the relatively constant temperature and environment in the body, the natural frequency of the charging circuit 607 can remain constant after the implantation of the IPG 10 into the body.

The IPG 10 can include an energy storage device 608. The energy storage device 608, which can include the energy storage features, can be any device configured to store energy and can include, for example, one or several batteries, capacitors, fuel cells, or the like. In some embodiments, the energy storage device 608 can be configured to receive charging energy from the charging module 606.

Figure 7:
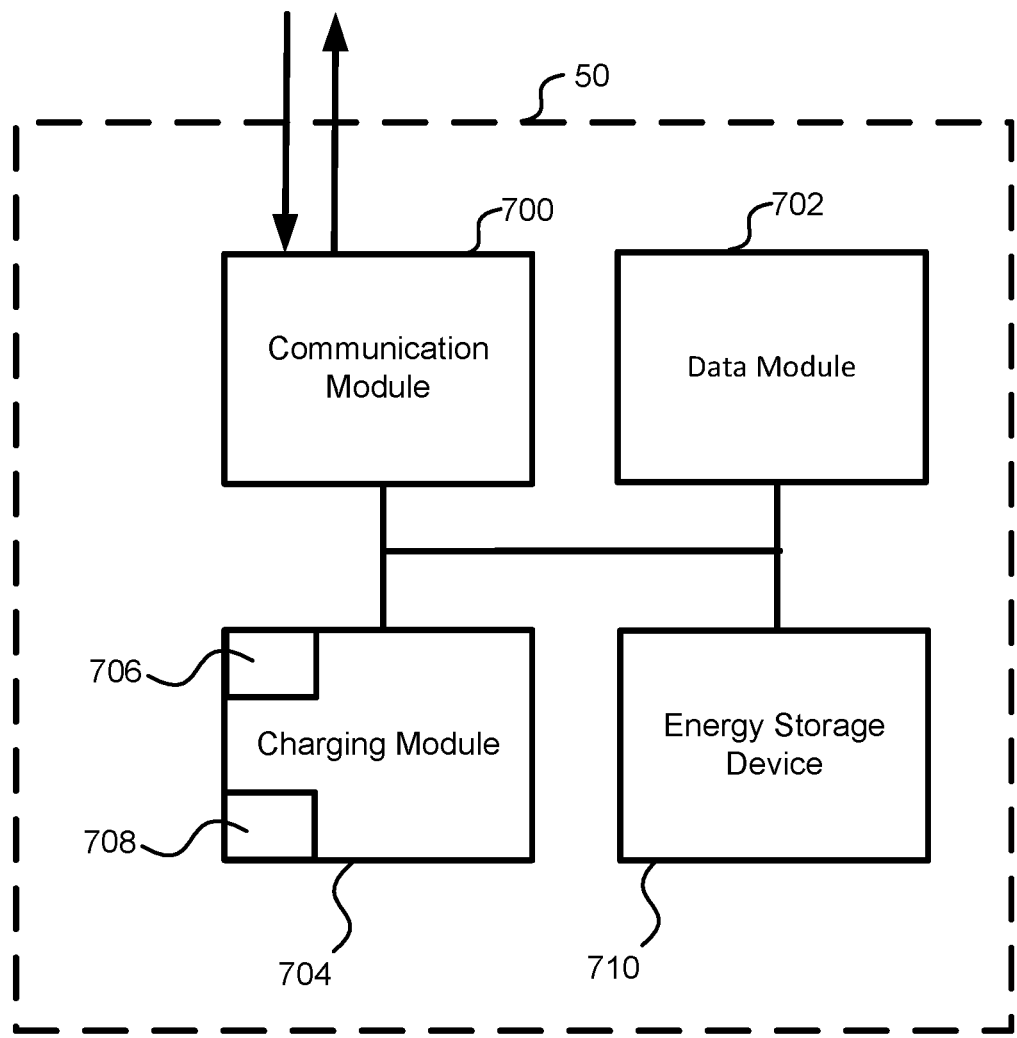
FIG. 7 shows a schematic illustration of one embodiment of the architecture of the charging device.

FIG. 7 shows a schematic illustration of one embodiment of the architecture of the charging device 50. In some embodiments, each of the components of the architecture of the charging device 50 can be implemented using the processor, memory, and/or other hardware component of the charging device 50. In some embodiments, the components of the architecture of the charging device 50 can include software that interacts with the hardware of the charging device 50 to achieve a desired outcome, and the components of the architecture of the charging device 50 can be located within the housing 51.

In some embodiments, charging device 50 can include, for example, a communication module 600. The communication module 700 can be configured to send data to and receive data from other components and/or devices of the exemplary nerve stimulation system including, for example, the clinician programmer 60, the IPG 10, and/or the patient remote 70. In some embodiments, the communication module 700 can include one or several antennas and software configured to control the one or several antennas to send information to and receive information from one or several of the other components of the CD 50. In some embodiments, for example, when connecting with the IPG 10, the communications module 700 can be configured to receive data identifying the IPG 10 and/or characterizing one or several attributes of the IPG 10. In some embodiments, this information can be, for example, a number uniquely identifying the IPG 10 such as, for example, a serial number, or the like. In some embodiments, this data can characterize one or several attributes of the IPG 10 such as, for example, the natural frequency of the charging module 606 of the IPG 10 and/or of one or several components of the charging module 606 of the IPG.

The CD 50 can further include a data module 702. The data module 702 can be configured to manage data relating to the identity and properties of the IPG 10. In some embodiments, the data module can include one or several database that can, for example, include information relating to the IPG 10 such as, for example, the identification of the IPG 10, one or several properties of the IPG 10, or the like. In one embodiment, for example, the data module can comprise a database including one or several IPG 10 identifiers such as serial numbers for those one or several IPGs 10. In some embodiments, the data module 702 can further include characterization data associated with some or all of the one or several IPGs 10 identified in the data module 702. In some embodiments, for example, this characterization data can include the identification of the natural frequency of charging circuit 607 of the IPG 10. In some embodiments, this characterization data can be received from the IPG 10 and/or can be generated by the CD 50 in response to interactions with the IPG 10.

The CD 50 can include a charging module 704. In some embodiments, the charging module 704 can be configured to control and/or monitor the charging/recharging of the IPG 10. In some embodiments, for example, the charging module 704 can include one or several features configured to provide energy for recharging the IPG 10 such as, for example, one or several inductive coils/features that can interact with one or several inductive coils/features of the IPG 10 to create an inductive coupling to thereby recharge the IPG 10. In some embodiments, the charging module 704 can include hardware and/or software configured to monitor the charging of the IPG 10 including, for example, the charging coil assembly 15.

The charging module 704 of the CD 50 can include a charging circuit 706, also referred to herein as the resonant circuit 706, the primary charging circuit 706, the primary resonant circuit 706, the transmitter charging circuit 706, or the transmitter resonant circuit 706. In some embodiments, the charging circuit 706 can comprise, for example, at least one of: an inductor; a capacitor; or a resistor. The charging circuit 607 can be characterized by a natural frequency, which natural frequency can be fixed or variable. In some embodiments, the natural frequency of the charging circuit 706 can be varied by the selective switched connection of one or several capacitors to the charging circuit 706. In some embodiments, the natural frequency of the charging circuit 706 can be varied by changing the inductance of one or several inductors in the charging circuit 706. In some embodiments, the inductance of these one or several inductors can be changed by changing the electrical saturation of a core, such as a ferritic core of the inductors via, for example, the changing of a voltage or a current, such as a DC current, passing through the core of the inductor.

In some embodiments, the charging module 704 can include a driver 708. The driver 708 can be, for example, a non-class E driver, and in some embodiments, the driver 708 can be a class E driver, and specifically can be a microprocessor controlled class E driver as disclosed in U.S. patent application Ser. No. 14/446,294, filed on Jul. 29, 2014, the entirety of which is hereby incorporated by reference herein.

In some embodiments, the driver 708 can be configured to provide electrical pulses to the resonant circuit 706 to thereby charge the IPG 10. In some embodiments, the driver 708 can be further configured to provide these pulses at a frequency corresponding to the natural frequency of the resonant circuit 706. Thus, in some embodiments, the natural frequency of the resonant circuit 706 of the CD 50 can be determined by determining the frequency with which the driver 708 is providing pulses to the resonant circuit 706.

The CD 50 can include an energy storage device 710. The energy storage device 710 can be any device and/or features configured to store energy and can include, for example, one or several batteries, capacitors, fuel cells, or the like. In some embodiments, the energy storage device 710 can be configured to provide charging energy to the charging module 704 for charging of the IPG 10.

Figure 8:
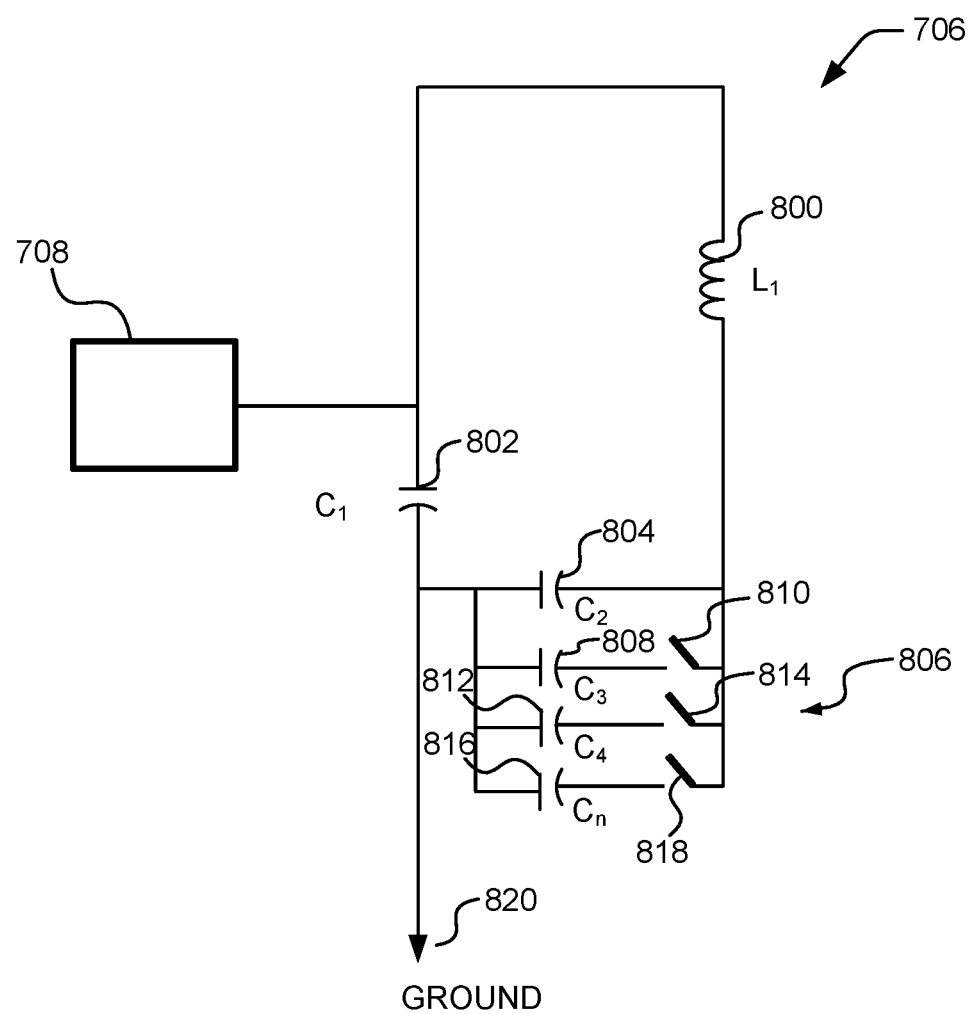
FIG. 8 shows a schematic illustration of one embodiment of a charging circuit including a plurality of switchably coupleable capacitors.

FIG. 8 is a schematic illustration of one embodiment of the charging circuit 706 of the charging module 704 of the CD 50. As seen in FIG. 8, the charging circuit 706 is connected to the driver 708. The charging circuit 706 includes an inductor 800 in parallel with an optional first capacitor 802, and the inductor 800 is in series with a second capacitor 804. In some embodiments, the first capacitor 802 can be included in the charging circuit 706, for example, when the driver 708 comprises a class E driver. The charging circuit can further include ground 820.

The charging circuit 706 additionally includes a capacitor array 806 comprising a plurality of capacitors. In some embodiments, the plurality of capacitors forming the array 806 are switchably connectable or coupleable with the charging circuit 706 such that each of the capacitors of the array 806 is electrically coupled or connected to charging circuit 706 when a switch associated with each capacitor of the array 806 is closed. Similarly, in some embodiments, the plurality of capacitors forming the array 806 are switchably connectable with the charging circuit 706 such that each of the capacitors of the array 806 is electrically disconnected to charging circuit 706 when a switch associated with each capacitor of the array 806 is open.

The array 806 can be positioned such that when the capacitors in the array 806 are electrically connected to the charging circuit 706, these capacitors are in parallel with the second capacitor 804 and are in series with the inductor 800. Through this arrangement, the selective coupling of the capacitors of the array 806 can change the natural frequency of the charging circuit 706.

The array 806 can include, for example, a first array capacitor 808 switchably coupleable to the charging circuit 706 via a first switch 810, a second array capacitor 812 switchably coupleable to the charging circuit 706 via a second switch 814, and a third array capacitor 816 switchably coupleable to the charging circuit 706 via a third switch 818. In some embodiments, the switches 810, 814, 818 can be controllably connected to the processor of the charger 50 such that control signals generated by the processor can result in the opening and/or closing of one or several of the switches 810, 814, 818. In some embodiments, these switches 810, 814, 818 can each comprise one or several transistors such as field-effect transistors (FET) such as, for example, a metal-oxide-semiconductor field-effect transistor (MOSFET).

Although the embodiment of FIG. 8 depicts three array capacitors 808, 812, 816, the array 806 can include more or fewer capacitors than shown in FIG. 8. In some embodiments, the number of capacitors can be selected to provide, for example, a desired number of different achievable natural frequencies of the charging circuit. In some embodiments, this desired number of different achievable natural frequencies can be selected based on, for example, manufacturing tolerances, range of expected frequency shifts from implantation, or the like.

The array capacitors 808, 812, 816 can comprise a variety of capacitances. In some embodiments, the capacitance of the array capacitors 808, 812, 816 can be selected to provide a desired range of possible natural frequencies of the charging circuit 706. In some embodiments, for example, the array 806 can be configured to allow the natural frequency of the charging circuit 706 to be adjusted within a range of approximately 50 Hz, approximately 30 Hz, approximately 20 Hz, approximately 10 Hz, approximately 5 Hz, between 0 and 10 Hz, between 0 and 20 Hz, between 0 and 30 Hz, between 0 and 50 Hz, and/or any other or intermediate range of frequencies. As used herein, "approximately" refers to a range of values extending +/−10 percent of the associated value around that associated value. In some embodiments, for example, the array 806 can allow adjustment of the natural frequency of the charging circuit 706 between 100 Hz and 150 Hz, between 110 Hz and 140 Hz, between 119 Hz and 130 Hz, between 120 Hz and 130 Hz, and/or between any other or intermediate frequencies.

In some embodiments, the array capacitors can be selected to, for example, provide a plurality of equal and/or approximately equal changes in the natural frequencies of the charging circuit 706. In one embodiment, for example, in which the array 806 includes three array capacitors 808, 812, 816, the capacitances of these three array capacitors 808, 812, 816 can be selected to provide approximately eight equal separated natural frequencies of the charging circuit. Thus, in embodiments in which the array 806 provides approximately 10 Hz of natural frequency adjustment to the charging circuit 706, the capacitances can be selected such that each of these eight natural frequencies is separated by a step of between 1 Hz and 2 Hz or of approximately 1.25 Hz from its one or several adjacent natural frequencies.

Figure 9:
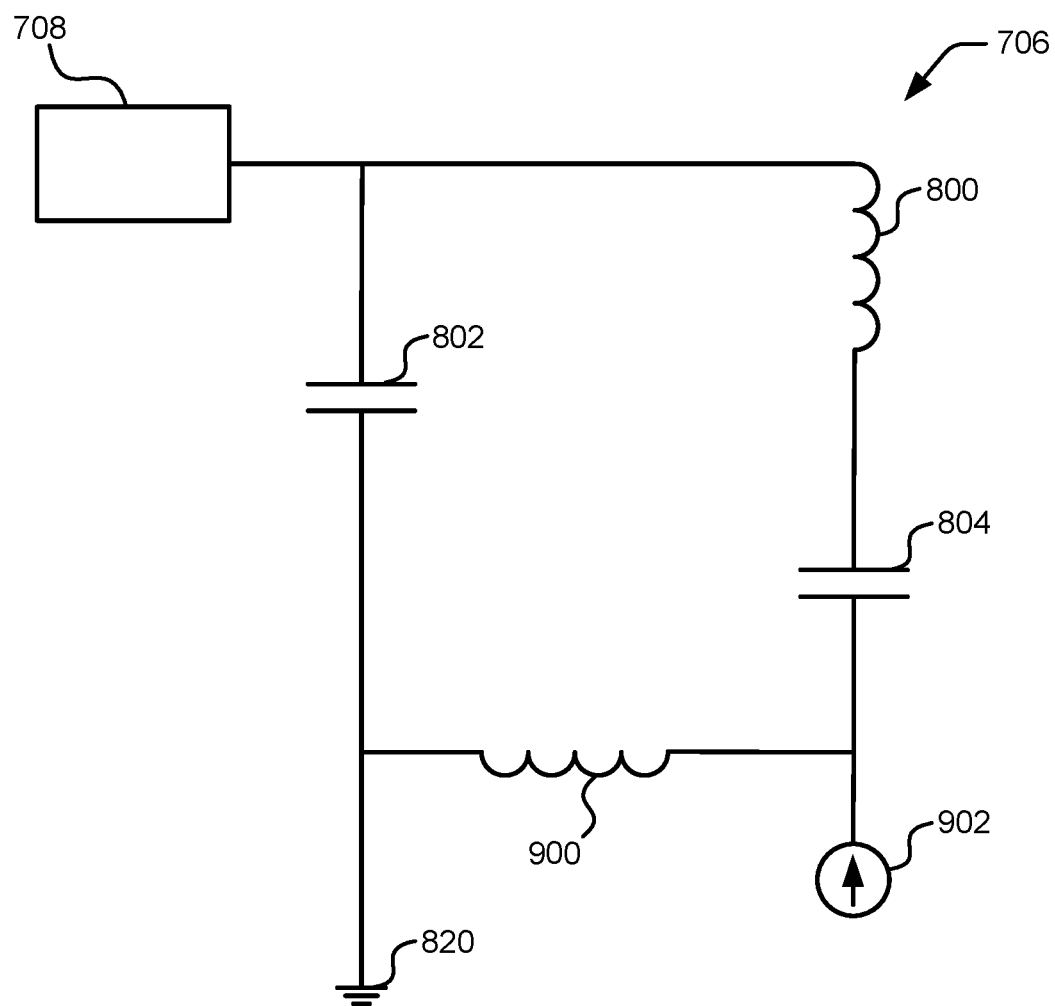
FIG. 9 shows a schematic illustration of one embodiment of a charging circuit including a variable inductance inductor.

FIG. 9 is a schematic illustration of another embodiment of the charging circuit 706 of the charging module 704 of the CD 50. As seen in FIG. 9, the charging circuit 706 is connected to the driver 708. The charging circuit 706 includes an inductor 800 in parallel with an optional first capacitor 802, and the inductor 800 is in series with a second capacitor 804. In some embodiments, the first capacitor 802 can be included in the charging circuit 706, for example, when the driver 708 comprises a class E driver. The charging circuit 706 can further include ground 820.

The charging circuit 706 can further include a second inductor 900. In some embodiments, the second inductor 900 can be positioned in series with the inductor 800. The second inductor 900 can be electrically coupled to a current source 902 and/or voltage source. In some embodiments, the current source 902 and/or the voltage source can be controlled to apply a different current and/or voltage to second inductor 902 to change the inductance of the second inductor 902 to thereby affect the natural frequency of the resonant circuit 706. In some embodiments, this change in voltage and/or current applied to the second inductor 900 can result in a change in the saturation level of the core of the second inductor 900, which core can be a ferritic core. In some embodiments, this change in the saturation of the core of the second inductor 900 can change the natural frequency of the resonant circuit 706 from a first natural frequency to a second natural frequency.

Figure 10:
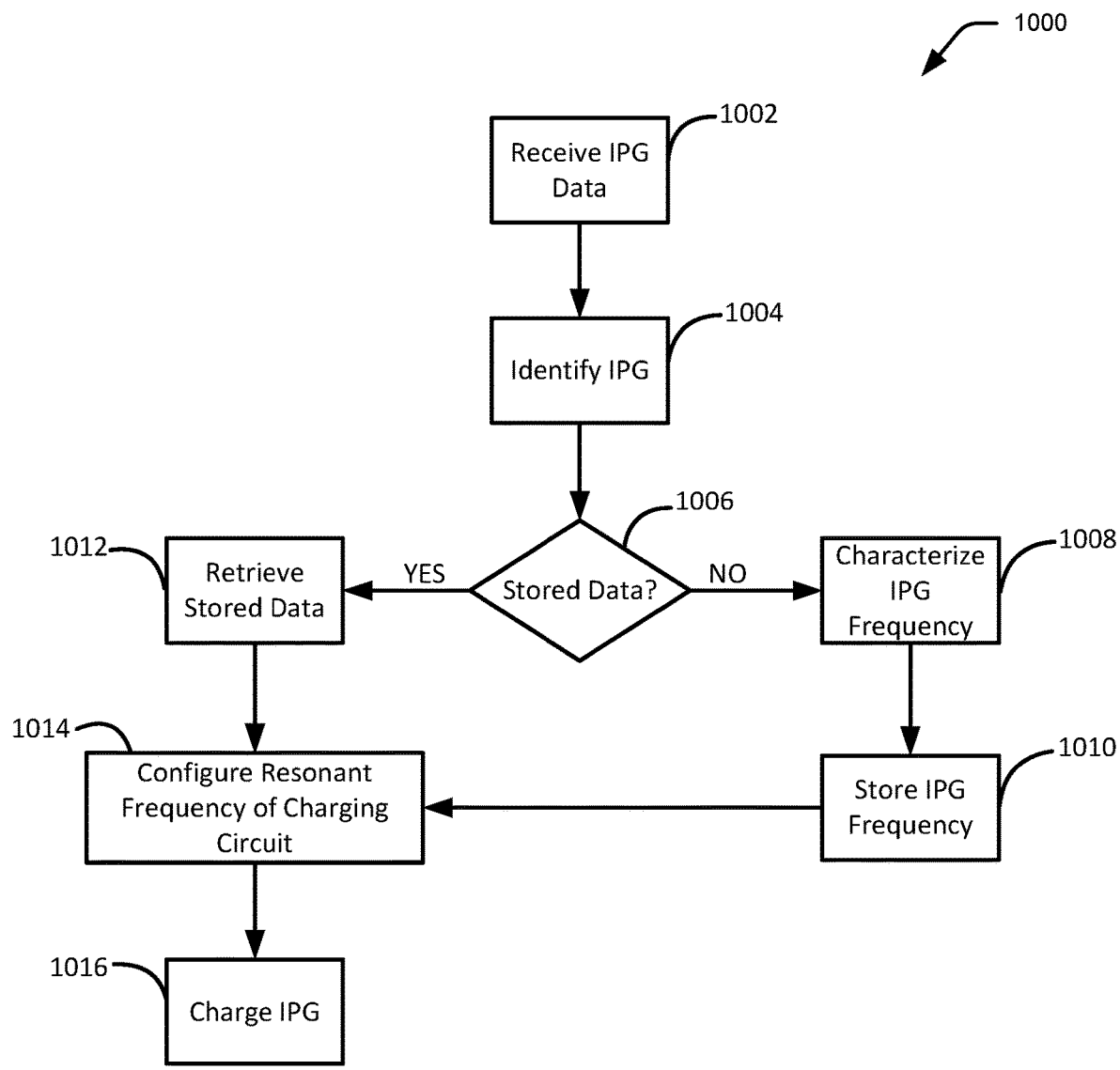
FIG. 10 is a flowchart illustrating one embodiment of a process for dynamic modulation of the natural frequency of a charging circuit.

FIG. 10 is a flowchart illustrating one embodiment of a process 1000 for dynamic modulation of the natural frequency of the charging circuit 706 of the CD 50 for management of wireless charging. The process 1000 can be performed by the CD 50. The process 1000 begins at block 1002 wherein IPG data is received. The IPG data can be received by the CD 50 via the communication module 700 of the CD 50 from the communication module 600 of the IPG 10. In some embodiments, the IPG data can include an identifier and can identify the IPG 10, and can, in some embodiments, uniquely identify the IPG 10. In some embodiments, the IPG data can further include characterization data characterizing, for example, the natural frequency of the charging circuit 607 of the IPG 10.

After the IPG data has been received, the process 1000 proceeds to block 1004 wherein the IPG is identified. In some embodiments, the identification of the IPG can include the extraction of identification information from the IPG data. In some embodiments, this can be performed by a processor of the CD 50 and can be performed by, for example, a processor associated with the data module 702.

After the IPG 10 has been identified, the process 1000 proceeds to decision state 1006 wherein it is determined if there is stored data for the identified IPG 10. In some embodiments, this story data can include, for example, characterization data characterizing the natural frequency of the charging circuit 607 of the IPG 10. In some embodiments, the determination of whether there is stored data can include querying the data module 702 and/or one or several databases of the data module for information relating to the IPG 10 identified at block 1004.

If the CD 50 does not include stored data relating to that IPG 10 identified and block 1004, the process 1000 proceeds to block 1008 wherein the IPG 10 is characterized, and specifically wherein a natural frequency of the charging circuit 607 of the IPG 10 is characterized. In some embodiments, this characterization can include the selective modulation of the natural frequency of the charging circuit 706 of the CD 50. In some embodiments, this selective modulation can be iteratively performed. In some embodiments, information relating to the effectiveness of the coupling between the charging circuit 706 of the CD 50 and the charging circuit 607 of the IPG 10 can be generated by the CD 50 and/or can be received from the IPG 10. Based on this information and, in some embodiments, the number of iterations of the selective modulation of the natural frequency of the charging circuit 706 of the CD 50, a natural frequency of the IPG 10 can be identified.

In some embodiments, the IPG 10 can be characterized at the time of assembly at, for example, the factory in which the IPG 10 is assembled. In such embodiments, the IPG 10 can provide data identifying the IPG 10, and/or identifying the natural frequency of the IPG 10 to the CD 50. In some embodiments, the IPG 10 can be characterized after implantation into the body of the patient. In some embodiments, the IPG 10 can be characterized multiple times after implantation into the body of the patient, and in some embodiments, the IPG 10 can be characterized a single time after implantation. In some embodiments, for example, the natural frequency of the IPG 10 can remain constant after the implantation of the IPG 10 into the body of the patient, and thus a one-time characterization of the IPG 10 after implantation can be adequate for coupling between the CD 50 and the IPG 10.

After the IPG 10 has been characterized, and specifically after the natural frequency of the IPG 10 has been characterized, the process 1000 proceeds to block 1010 wherein the natural frequency of the IPG 10, and specifically of the charging circuit 607 of the IPG 10 is stored. In some embodiments, this natural frequency can be stored in the data module 702 of the CD 50, and more specifically can be stored in the database in the data module 702 of the CD 50.

Returning again to decision state 1006, if it is determined that the CD 50 has stored data for the IPG 10 identified at block 1004, then the process 1000 proceeds to block 1012 wherein the stored data is retrieved. In some embodiments, the store data can be retrieved from the data module 702, and particularly from one of the databases of the data module 702.

After the stored data has been retrieved, or returning to block 1010 after the IPG frequency has been stored, the process 1000 proceeds to block 1014 wherein the resonant frequency of the charging circuit is configured. In some embodiments, this can include changing and/or modifying the natural frequency of the charging circuit such that the natural frequency of the charging circuit matches and/or corresponds to the natural frequency of the IPG 10 either as characterized in block 1008 or as identified in the retrieved stored data of block 1012.

After the resonant frequency of the charging circuit has been configured, the process 1000 proceeds to block 1016 wherein the IPG 10 is charged. In some embodiments, the IPG 10 can be charged by the delivery of power to the charging circuit by the driver 708.

Figure 11:
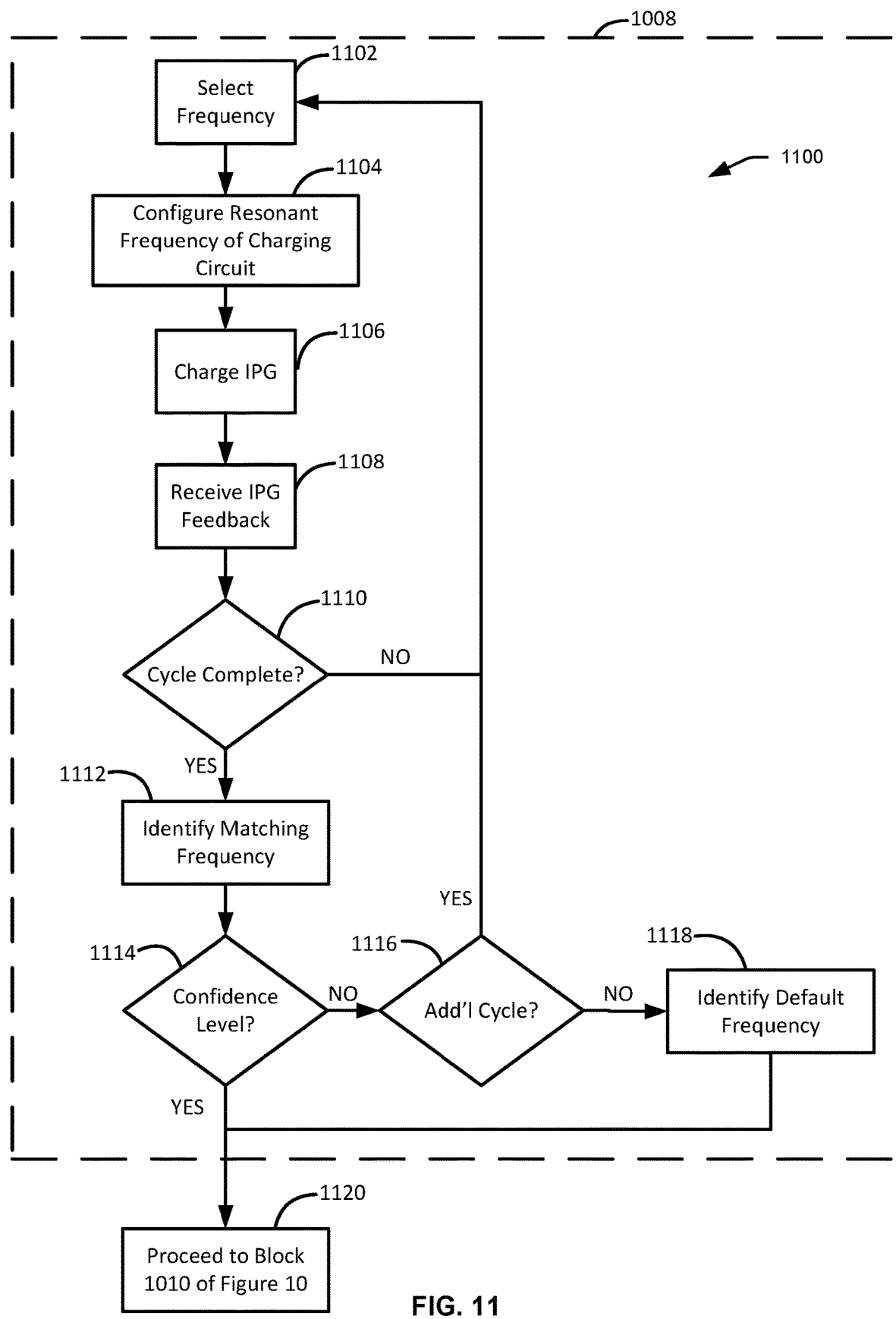
FIG. 11 is a flowchart illustrating one embodiment of a process for characterizing an IPG.

With reference now to FIG. 11, a flowchart illustrating one embodiment of a process 1100 for characterizing an IP 10 is shown. The process 1100 can be performed as part of, or in the place of the step depicted by block 1008 of FIG. 10. The process begins at block 1102 wherein a frequency is selected. In some embodiments, this specifically includes a selection of a natural frequency for the charging circuit 706 of the CD 50. In some embodiments, this frequency can be selected by, for example, selecting a switching configuration to electrically couple a desired number of array capacitors 808, 812, 816 to the charging circuit 706, and generating one or several control signals to cause switching corresponding to the selected switching configuration. Alternatively, this frequency can be selected by, for example, selecting an inductance of an inductor of the charging circuit 706 and generating one or several control signals to achieve the selected inductance. This selected frequency can be one of a plurality of natural frequencies of the charging circuit 706.

After the frequency has been selected, the process 1100 proceeds to block 1104 wherein the resonant frequency of the charging circuit 706 of the CD 50 is configured to match the selected frequency of block 1102. In some embodiments, this can include, for example, providing the control signals generated in block 1102 to components of the charging circuit 706 of the CD 50. In some embodiments, the components, such as, for example, switches 810, 814, 818 and/or the second inductor 900, can receive the control signals and can act according to those receipts control signals.

After the resonant frequency of the charging circuit has been configured to match the frequency selected in block 1102, the process 1100 proceeds to block 1106 wherein the IPG 10 is charged. In some embodiments, the charging of the IPG can include the control of the driver 708 to send one or several electrical pulses to the charging circuit 706 to cause resonance within the charging circuit 706 to thereby be inductively coupled with the charging circuit 607 of the IPG 10. In some embodiments, the driver 708 can provide one or several electrical pulses to the charging circuit 706 of the CD 50 at a frequency corresponding to the resonant frequency of the charging circuit 706 of the CD 50.

After or during the charging of the IPG, the process 1100 can proceed to block 1108 wherein charging efficiency feedback is received and/or generated. In some embodiments, this feedback can indicate the effectiveness of the inductive coupling between the charging circuits 607, 706 which can likewise indicate the degree to which the natural frequency of the charging circuit 706 of the CD 50 matches and/or corresponds to the natural frequency of the charging circuit 607 of the IPG 10. In some embodiments, this feedback can include and/or can be based on data indicative of the amount of power received at the IPG 10 and/or the amount of power provided to the charging circuit 706 of the CD 50. In some embodiments, this feedback can be received by the communication module 700 of the CD 50 from the communication module 600 of the IPG 10.

After the charging efficiency feedback has been received, the process 1100 proceeds to decision state 1110 wherein it is determined if the characterization cycle is complete. In some embodiments, the characterization cycle can be complete when the charging circuit 706 of the CD 50 has been configured at a desired number of natural frequencies and charging of the IPG 10 has been performed at each of those natural frequencies. In some embodiments, the cycle is completed when, the charging circuit 706 of the CD 50 is iteratively configured a desired number of times at each of the desired number of natural frequencies and the IPG is charged at each of the desired number of natural frequencies a desired number of times. If it is determined that the cycle is not complete such as, for example, when configuration of the charging circuit 706 and the desired number frequencies has not been completed and/or when the desired number of iterations has not been attained, the process 1100 returns to block 1102 and proceeds as outlined above.

If it is determined that the cycle is complete, then the process 1100 proceeds to block 1112 wherein the best performing frequency of the CD 50 is selected. In some embodiments, this best-performing's frequency can be selected based on the feedback received in block 1108. In some embodiments, the best-performing frequency of the CD 50 can be the natural frequency of the charging circuit 706 of the CD 50 that most efficiently inductively coupled with the charging circuit 607 of the IPG 10. In some embodiments, the identified natural frequency can be one of a plurality of natural frequencies. In some embodiments, the identified matching frequency is the one of the plurality of natural frequencies that best matches the natural frequency of the charging circuit 607 of the IPG 10.

After the matching frequency has been identified, the process 1100 proceeds to decision state 1114 wherein it is determined if a desired confidence level is achieved. In some embodiments, this can include applying one or several statistical methods or techniques to the IPG feedback received in block 1108. In some embodiments, these can be used to determine the statistical confidence that the matching frequency identified and block 1112 is in fact the frequency of the CD 50 that best matches the natural frequency of the IPG 10. This determination can be performed by, for example, the data module 702 or the charging module 704 of the CD 50. In some embodiments, this can include determining if the identified matching frequency matches the natural frequency of the charging circuit 607 of the IPG 10 over a statistically significant number of iterations.

If it is determined that the confidence level is not attained, then the process 1100 proceeds to block 1116 wherein it is determined if an additional cycle should be performed. In some embodiments, the additional cycle can include one or several additional iterations of configuring the charging circuit 706 of the CD 50 at one or several selected natural frequencies and charging the IPG 10 at those one or several selected natural frequencies. In some embodiments, the one or several selected natural frequencies of the additional cycle can be the same selected natural frequencies applied in previous cycles or one or several different natural frequencies that have been selected and applied in previous cycles. In some embodiments, determining whether to perform an additional cycle can include comparing the number of already completed and/or performed cycles to a maximum number of allowable cycles and determining if the number of already performed cycles meets or exceeds the maximum number of allowable cycles. Alternatively, in some embodiments, the determination of whether to perform an additional cycle can include determining whether convergence in the feedback and/or identified matching frequencies is occurring such that one or several additional cycles would likely result in the identification of a matching frequency having a desired confidence level. This determination of whether to perform an additional cycle can be made by the processor of the CD 50, and specifically by one or more of the data module 702 in the charging module 706 of the CD 50.

If it is determined to perform an additional cycle, then the process 1100 returns to block 1102 and proceeds as outlined above. If it is determined not to perform an additional cycle, then the process 1100 proceeds to block 1118 wherein a default frequency is identified. In some embodiments, the default frequency can be a natural frequency of the charging circuit 706 of the CD that can be selected when no matching frequency achieving the desired confidence level is identified. In some embodiments, one or several default frequencies can be stored in the data module 702 and the identification of a default frequency as indicated in block 1118 can include retrieving one or several default frequencies from the data module 702.

After the default frequency has been identified or, returning again to decision state 1114, if it is determined that the desired confidence level is achieved, then the process 1100 proceeds to block 1120 and continues to block 1010 of FIG. 10.

Figure 12:
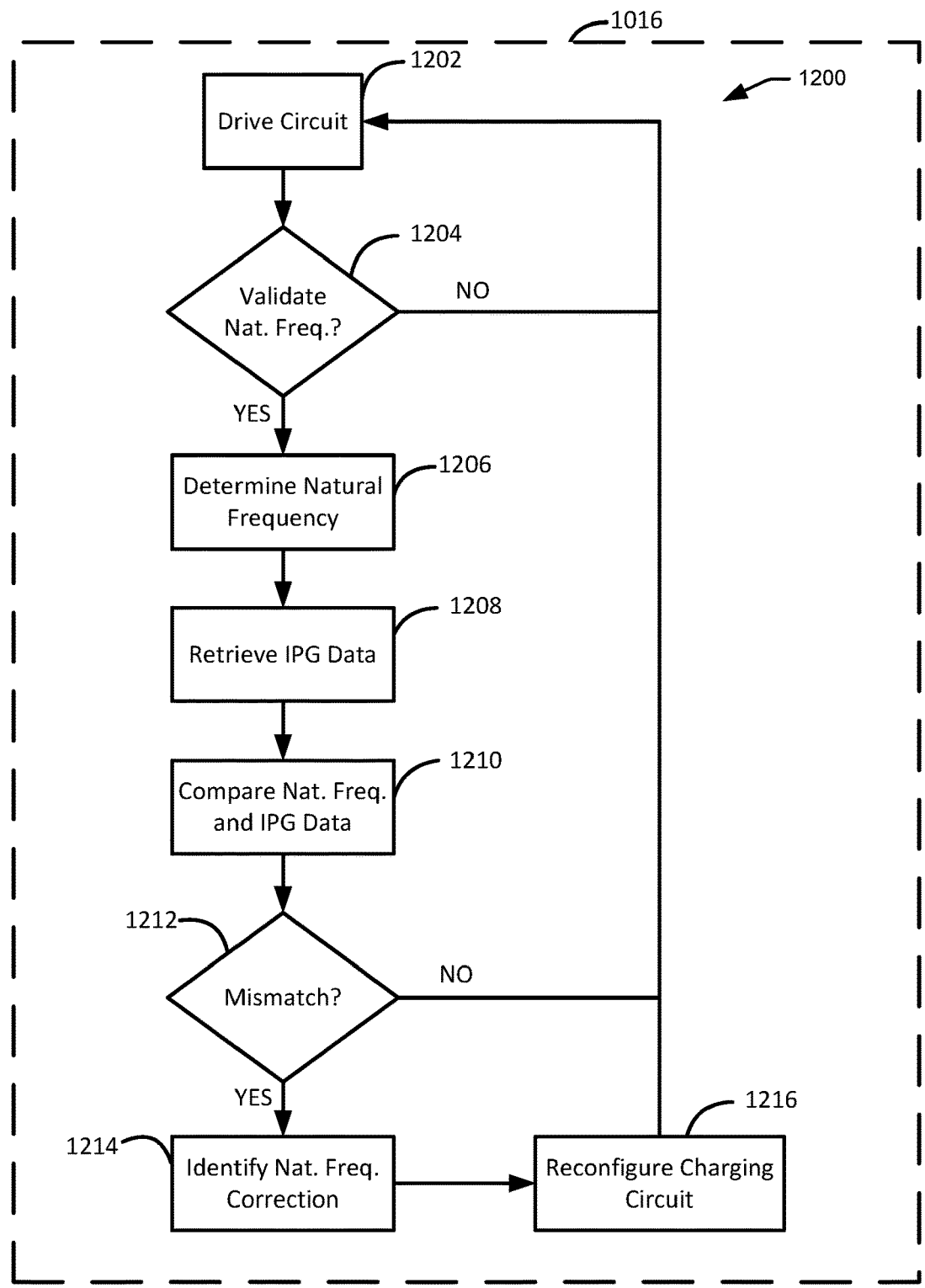
FIG. 12 is a flowchart illustrating one embodiment of a process for dynamically controlling the natural frequency of the charging circuit of the charging device.

With reference not to FIG. 12, a flowchart illustrating one embodiment of a process 1200 for dynamically controlling the natural frequency of the charging circuit 706 of the charging device 50 is shown. In some embodiments, the process 1200 can be performed using stored data identifying the natural frequency of the IPG 10, and specifically identifying the natural frequency of the charging circuit 607 of the IPG 10. In some embodiments, the use of stored IPG data can adequately characterize the natural frequency of the IPG 10 as the natural frequency of the IPG 10 can be constant after implantation. In some embodiments, controlling the natural frequency of the charging circuit 706 of the CD 50 with stored IPG data can improve system performance as compared to control of the natural frequency of the charging circuit 706 based on real-time data received from the IPG 10 as stored IPG data can be accessed regardless of the existence of a communicating connection between the IPG 10 and the CD 50 and as use of stored IPG data can allow quicker processing times and thus more responsive control of the natural frequency of the charging circuit 706 of the CD 50.

The process 1200 can be performed as part of, or in the place of the step depicted by block 1016 of FIG. 10. The process begins at block 1202 wherein the charging circuit 706 of the CD 50 is driven by, for example, the driver 708. In some embodiments, the driver 708 is configured to drive the charging circuit 706 of the CD 50 at the natural frequency of the charging circuit 706 of the CD 50.

After the charging circuit 706 is driven, or while the charging circuit is being driven, the process 1200 proceeds to block 1204 wherein it is determined whether to validate the natural frequency of the charging circuit 706 of the CD 50. In some embodiments, this validation can be periodically performed in which case the determination of whether to validate the natural frequency of the charging circuit 706 of the CD 50 can include determining whether the desired amount of time has passed since the last validation the natural frequency. In some embodiments, the natural frequency can be validated when a trigger signal is received from, for example, the IPG 10. In some embodiments, the trigger signal can be generated and sent by the IPG 10 when a change in charging efficiency is determined. If it is determined not to validate the natural frequency of the charging circuit 706, the process 1200 returns to block 1202 and proceeds as outlined above.

If it is determined to validate the natural frequency of the charging circuit 706, than the process 1200 proceeds to block 1206 wherein the natural frequency of the charging circuit 706 of the CD 50 is determined. In some embodiments, the natural frequency of the charging circuit 706 can be determined by determining the driving frequency of the driver 708. As previously mentioned, in some embodiments, the driver 708 can be configured to provide electrical pulses to the charging circuit 706 of the CD 50 at the natural frequency of the charging circuit 706. In such an embodiment, the frequency with which the driver 708 drives the charging circuit 706 can be retrieved from the driver 708 and the natural frequency of the charging circuit 706 can thereby be determined. Alternatively, in some embodiments, the natural frequency of the charging circuit 706 can be determined by termination of the driving of the charging circuit 706 by the driver 708 and the detection of frequency of ringing of the charging circuit 706. In some embodiments, this frequency of ringing corresponds to the natural frequency of the charging circuit.

After the natural frequency of the charging circuit 706 has been determined, the process 1200 proceeds to block 1208 wherein IPG data is retrieved. In some embodiments, the IPG data can include the characterization data for the IPG 10 which identifies the natural frequency of the IPG. In some embodiments, the IPG data can be retrieved from the data module 702, and specifically from one of the databases of the database module 702. In some embodiments, the IPG data can be generated by the characterization of the IPG 10 as discussed with reference to FIG. 11.

After the IPG data has been retrieved, the process 1200 proceeds to block 1210 wherein the natural frequency of the charging circuit 706 is determined and block 1206 is compared to the IPG data. In some embodiments this can include, for example, determining whether the natural frequency of the charging circuit 706 is greater than, less than, or equal to the natural frequency of the charging circuit 607 of the IPG 10 as identified in the IPG data. In some embodiments, a first value can be associated with the natural frequency of the charging circuit 706 when the natural frequency of the charging circuit 706 is greater than the natural frequency of the charging circuit 607 of the IPG 10, a second value can be associated with the natural frequency of the charging circuit 706 when the natural frequency of the charging circuit 706 is less than the natural frequency of the charging circuit 607 of the IPG 10, and the third value can be associated with the natural frequency of the charging circuit 706 when the natural frequency of the charging circuit 706 is equal to the natural frequency of the charging circuit 607 of the IPG 10.

After the natural frequency of the charging circuit 706 of the CD 50 is compared to the natural frequency of the charging circuit 607 of the IPG data as indicated in the IPG data, the process 1200 proceeds to decision state 1212 wherein it is determined if there is a mismatch between the natural frequency of the charging circuit 706 of the CD 50 and the natural frequency of the charging circuit 607 of the IPG 10. In some embodiments, this can be based on the results of the comparison of block 1210, and in some particular embodiments, this determination can include determining which of the first, second, and third values was associated with the natural frequency of the charging circuit 706 and block 1210. If it is determined that there is no mismatch between the natural frequency of the charging circuit 706 of the CD 50 and the IPG data, then the process 1200 returns to block 1202 and proceeds as outlined above.

If it is determined that there is a mismatch between the natural frequency of the charging circuit 706 of the CD 50 and the IPG data, then the process 1200 proceeds to block 1214 where the natural frequency correction is identified. In some embodiments, this can include identifying a change in the natural frequency of the charging circuit 706 that would result in a match between the natural frequency of the charging circuit 706 and the IPG data and/or minimize the difference between the natural frequency of charging circuit 706 and the IPG data. This determination can be based on the comparison performed in block 1210. In some embodiments, identifying the natural frequency correction in block 1214 can further include generating one or several control signals to change the natural frequency of the charging circuit 706 to thereby correct the natural frequency of the charging circuit 706.

After the natural frequency correction has been identified, the process 1200 proceeds to block 1216 wherein the charging circuit 706 of the CD 50 is reconfigured according to the natural frequency correction identified at block 1214. In some embodiments, this can include sending the control signals generated in block 1214 to the charging circuit 706 to thereby change the opened and closed state of one or several of the switches 810, 814, 818 and/or the inductance of the second inductor 900.

After the charging circuit has been reconfigured, the process 1200 can return to block 1202 and proceed as outlined above. In some embodiments, the process 1200 can be performed until charging of the IPG 10 is complete. In some embodiments, the completeness of the charging of the IPG 10 can be determined based on one or several signals received from the IPG 10 by the communication module 700 of the CD 50.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A charger for coupling with an implantable neurostimulator for delivering one or more electrical pulses to a target region within a patient's body, the charger comprising:
   a memory;

a power source for storing electrical energy;
a resonant circuit, wherein the resonant circuit is configurable to a plurality of natural frequencies;
a driver coupled to the power source and the resonant circuit, wherein the driver is configured to power the resonant circuit; and
a processor coupled to the resonant circuit to control the natural frequency of the resonant circuit, wherein the processor is configured to control the natural frequency of the resonant circuit according to data associated with the implantable neurostimulator and stored in the memory, wherein controlling the natural frequency of the resonant circuit according to data associated with the implantable neurostimulator comprises:
receiving identifying data from the implantable neurostimulator; and
retrieving characterization data, wherein the characterization data identifies a natural frequency of a resonant circuit of the implantable neurostimulator.

2. The charger of claim 1, wherein controlling the natural frequency of the resonant circuit according to data associated with the implantable neurostimulator comprises:
detecting a first natural frequency of the resonant circuit of the charger;
comparing the first natural frequency of the resonant circuit of the charger to the characterization data; and
changing the natural frequency of the resonant circuit of the charger from the first natural frequency to a second natural frequency.

3. The charger of claim 2, wherein detecting the first natural frequency of the resonant circuit of the charger comprises at least one of: determining a driving frequency of the driver; or detecting ringing of the resonant circuit.

4. The charger of claim 2, wherein the second natural frequency corresponds to the characterization data.

5. The charger of claim 4, wherein the resonant circuit comprises:
an inductor;
a first capacitor coupled in series to the inductor; and
a plurality of capacitors switchably coupleable to the inductor, wherein the plurality of capacitors are each configured to be in parallel with the first capacitor when switchably coupled to the inductor.

6. The charger of claim 5, wherein the plurality of capacitors comprises three capacitors.

7. The charger of claim 6, wherein each of the plurality of capacitors is switchably coupleable to the inductor via a transistor.

8. The charger of claim 7, wherein the transistor is a field effect transistor.

9. The charger of claim 5, wherein changing the natural frequency of the resonant circuit of the charger from the first natural frequency to a second natural frequency comprises:
identifying a first switch configuration of the resonant circuit resulting in the first natural frequency;
identifying a second switch configuration of the resonant circuit resulting in the second natural frequency; and
generating a control signal to control at least one of: opening of at least one switch in the resonant circuit to disconnect at least one of the plurality of capacitors from the inductor; or closing of at least one switch in the resonant circuit to connect at least one of the plurality of capacitors from the inductor.

10. The charger of claim 4, wherein changing the natural frequency of the resonant circuit of the charger from the first natural frequency to a second natural frequency comprises:
identifying a first inductance of an inductor in the resonant circuit resulting in the first natural frequency;
identifying a second inductance of the inductor in the resonant circuit resulting in the second natural frequency; and
generating a control signal to change the inductance of the inductor from the first inductance to the second inductance.

11. The charger of claim 10, wherein changing the inductance of the inductor from the first inductance to the second inductance comprises changing a saturation level of a core of the inductor from a first saturation level to a second saturation level.

12. The charger of claim 11, wherein changing the saturation level of the core of the inductor from the first saturation level to the second saturation level comprises changing a voltage applied to the core of the inductor from a first voltage to a second voltage.

13. The charger of claim 4, wherein the first natural frequency is repeatedly detected.

14. The charger of claim 4, wherein the first natural frequency is periodically detected.

15. The charger of claim 4, wherein the natural frequency of the resonant circuit can be adjusted within a range of 20 Hz.

16. The charger of claim 4, wherein the natural frequency of the resonant circuit can be adjusted within a range of 10 Hz.

17. The charger of claim 4, wherein the natural frequency of the resonant circuit can be adjusted between approximately 119 Hz and 130 Hz.

18. The charger of claim 1, wherein the driver comprises a class-E driver.

19. A charger for coupling with an implantable neurostimulator for delivering one or more electrical pulses to a target region within a patient's body, the charger comprising:
a memory;
a power source for storing electrical energy;
a resonant circuit, wherein the resonant circuit is configurable to a plurality of natural frequencies;
a driver coupled to the power source and the resonant circuit, wherein the driver is configured to power the resonant circuit; and
a processor coupled to the resonant circuit to control the natural frequency of the resonant circuit, wherein the processor is configured to control the natural frequency of the resonant circuit according to data associated with the implantable neurostimulator and stored in the memory wherein the data associated with the implantable neurostimulator identifies the implantable neurostimulator and identifies a previously determined natural frequency of the implantable neurostimulator.

* * * * *